US009452005B2

(12) United States Patent
Appenzeller et al.

(10) Patent No.: US 9,452,005 B2
(45) Date of Patent: Sep. 27, 2016

(54) BONE FIXATION SYSTEM

(71) Applicant: DePuy Synthes Products, Inc., Raynham, MA (US)

(72) Inventors: Andreas Appenzeller, Oberdorf (CH); Daniel Fluri, Oberdorf (CH); Johann Fierlbeck, Oberdorf (CH); Alfred Niederberger, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 316 days.

(21) Appl. No.: 13/832,364

(22) Filed: Mar. 15, 2013

(65) Prior Publication Data

US 2014/0058455 A1 Feb. 27, 2014

Related U.S. Application Data

(60) Provisional application No. 61/692,673, filed on Aug. 23, 2012.

(51) Int. Cl.
*A61B 17/80* (2006.01)
*A61B 17/86* (2006.01)

(52) U.S. Cl.
CPC ....... *A61B 17/8057* (2013.01); *A61B 17/8047* (2013.01); *A61B 17/8052* (2013.01); *A61B 17/8061* (2013.01); *A61B 17/8605* (2013.01); *A61B 17/869* (2013.01)

(58) Field of Classification Search
CPC .......... A61B 17/8057; A61B 17/8605; A61B 17/8615; A61B 17/862; A61B 17/8085; A61B 17/869
See application file for complete search history.

(56) References Cited

U.S. PATENT DOCUMENTS

| | | | |
|---|---|---|---|
| 4,429,690 | A | 2/1984 | Angelino-Pievani |
| 4,467,793 | A | 8/1984 | Ender |
| 5,281,225 | A | 1/1994 | Vicenzi |

(Continued)

FOREIGN PATENT DOCUMENTS

| | | |
|---|---|---|
| DE | 202005019277 | 2/2006 |
| EP | 0401650 | 12/1990 |

(Continued)

OTHER PUBLICATIONS

International Patent Application No. PCT/US2013/056345: International Search Report dated Oct. 23, 2013, 10 pages.

(Continued)

*Primary Examiner* — David Bates
*Assistant Examiner* — Olivia C Chang
(74) *Attorney, Agent, or Firm* — Baker & Hostetler LLP

(57) ABSTRACT

A bone fixation system has a bone implant with an implant body. The implant body defines an upper surface, a bone-facing surface spaced from the upper surface along a transverse direction, and at least one aperture defined by an inner wall. A bone fixation element is configured for insertion at least partially through the aperture. The bone fixation element defines a proximal end and a distal end spaced from the proximal end along a central axis. The bone fixation element has a head and a shaft that extends relative to the head toward the distal end. The head defines a first ridge, a second ridge spaced from the first ridge, and a groove disposed between the first and second ridges. The groove can receive at least a portion of the inner wall to couple the bone fixation element to the bone implant.

16 Claims, 15 Drawing Sheets

(56) References Cited

U.S. PATENT DOCUMENTS 5,324,307 A 6/1994 Jarrett et al.
5,725,532 A 3/1998 Shoemaker
5,913,896 A 6/1999 Boyle et al.
6,203,545 B1 3/2001 Stoffella
6,506,191 B1 1/2003 Joos
6,558,388 B1 5/2003 Bartsch et al.
7,776,076 B2 * 8/2010 Grady et al. .................. 606/291
8,172,884 B2 5/2012 Bouman
8,343,152 B2 * 1/2013 Gonzalez-Hernandez ..... 606/62
2003/0153918 A1 8/2003 Putnam et al.
2004/0236170 A1 11/2004 Kim
2005/0101961 A1 5/2005 Huebner et al.
2005/0136764 A1 6/2005 Sherman et al.
2005/0261688 A1 11/2005 Grady, Jr. et al.
2006/0009771 A1 1/2006 Orbay et al.
2006/0189992 A1 8/2006 Medoff
2006/0276793 A1 * 12/2006 Berry ................. A61B 17/8052 606/70
2007/0173834 A1 7/2007 Thakkar
2008/0065074 A1 3/2008 Yeung et al.
2008/0188899 A1 8/2008 Bottlang et al.
2008/0269745 A1 10/2008 Justin
2008/0281363 A1 11/2008 Ullman et al.
2010/0036430 A1 2/2010 Hartdegen et al.
2011/0009912 A1 1/2011 Gonzalez-Hernandez et al.
2011/0270312 A1 11/2011 Assell et al.
2011/0282393 A1 11/2011 Gerlach et al.
2012/0004690 A1 * 1/2012 Gonzalez-Hernandez ... 606/305
2012/0136396 A1 5/2012 Baker et al.
2012/0330365 A1 12/2012 Lin et al.
2014/0058391 A1 2/2014 Appenzeller et al.
2015/0018889 A1 1/2015 Schneider
2015/0223853 A1 8/2015 Appenzeller et al.

FOREIGN PATENT DOCUMENTS

EP 0743045 11/1996
EP 0873718 10/1998
EP 0882431 12/1998
FR 2722545 1/1996
FR 2728155 6/1996
WO WO 87/02572 5/1987
WO WO 98/33448 8/1998

OTHER PUBLICATIONS

International Patent Application No. PCT/US2013/056367: International Search Report dated Oct. 23, 2013, 10 pages.
International Patent Application No. PCT/US2013/056348: Invitation to Pay Additional Fees dated Oct. 23, 2013, 6 pages.
International Patent Application No. PCT/US2013/056374: International Search Report dated Nov. 5, 2013, 10 pages.
U.S. Appl. No. 13/832,518, filed Mar. 15, 2013, Appenzeller et al.
International Patent Application No. PCT/US2013/056348: International Search Report dated Jan. 17, 2014, 16 pages.

* cited by examiner 206
260
255
51
262
256
276

360
306
355
51
356
376
358

T
A
10
24
102
22
80
Θ
82
44
33
40
46
42
104
226

T
A
10
24
102
22
94a
96a
44
90
40
46
326
33
92
94b
91
42
96b
104

BONE FIXATION SYSTEM

CROSS-REFERENCE TO RELATED APPLICATIONS

This application claims the benefit of U.S. Provisional Application No. 61/692,673 filed Aug. 23, 2012, the entire disclosure of which is incorporated in this application for all purposes.

TECHNICAL FIELD

The present disclosure relates to a bone fixation system, and particularly to a bone implant and a bone fixation element, methods for coupling a bone implant to a bone fixation element, and methods for bone fixation.

BACKGROUND

Bone implants are designed to help heal bone fractures and/or replace damaged tissue. Principles that guide bone implant design include anatomic reduction of fracture fragments, stable fixation to improve tissue healing, minimal procedural invasiveness to preserve local blood supply, and early and pain-free mobilization so that the patient can return to normal function as soon as possible. These principles have guided the development of many examples of bone implants, such as bone plates, intramedullary nails, vertebral implants, etc., as well as screws and or anchors configured to hold the bone implant in the desired position at the intended tissue site.

SUMMARY

According to an embodiment of the present disclosure, a bone fixation system can include a bone implant and at least one bone fixation element. The bone implant can be elongate along a longitudinal direction. The bone implant includes an implant body that defines an upper surface, a bone-facing surface opposite the upper surface and spaced from the upper surface along a transverse direction that is perpendicular to the longitudinal direction, at least one aperture that extends through the implant body from the upper surface to the bone-facing surface. The at least one aperture is defined by an inner wall. The bone fixation element is configured to be inserted at least partially through the aperture into an underlying fixation site. The bone fixation element defines a proximal end and a distal end spaced from the proximal end along a central axis in a distal direction. The bone fixation element defines a bone fixation body having a head disposed at the proximal end and a shaft that extends relative to the head toward the distal end. The head defines a first ridge and a second ridge that is spaced from the first ridge along the distal direction, and a groove disposed between the first and second ridges. The groove is recessed into the head toward the central axis between the first and second ridges. The groove is configured to receive at least a portion of the inner wall to secure the bone fixation element to the bone implant.

BRIEF DESCRIPTION OF THE DRAWINGS

The foregoing summary, as well as the following detailed description of illustrative embodiments of the bone fixation system of the present disclosure, is better understood when read in conjunction with the appended drawings. It should be understood, however, that the present disclosure is not limited to the precise schematics and arrangements shown. In the drawings.

DETAILED DESCRIPTION OF ILLUSTRATIVE EMBODIMENTS

Referring to FIGS. 1A-1D, a bone fixation system 2 in accordance with one embodiment is configured to stabilize a bone that has been fractured at one or more fracture locations into a plurality of bone fragments. The bone fixation system 2 includes a bone implant 4 and a bone fixation element 6 configured for insertion at least partially through the bone implant 4 to secure the bone implant 4 to an underlying fixation site 8. The bone fixation element 6 includes a variable dimensioned profile that assists in advancing the bone fixation element 6 through the bone implant 4 in a transverse direction T relative to the bone implant 4 toward the fixation site 8, as well as coupling the bone fixation element 6 to the bone implant 4 (FIG. 1E).

The fixation site 8 can be a bone as illustrated, an implant, or a device configured to receive a bone fixation element. For instance, the fixation site 8 can be a pair of fixation sites that include a first fixation site 8*a* located on a first bone fragment 7*a* and a second fixation site 8*b* located on a second bone fragment 7*b*. The second bone fragment 7*b* is separated from the first bone fragment 7*a* by a fracture location FL. The fixation site 8 can be located at any anatomical location on a skeletal system. For instance, the fixation site 8 can be located on the skull, the vertebral column, any long bone, such as the humerus, femur, tibia, fibula, or any other location on the skeleton system where fixation is needed. The fixation site 8 can also be an additional implant, device or prosthesis configured to receive the bone fixation element therethrough for securement to the bone.

Figure 1A:
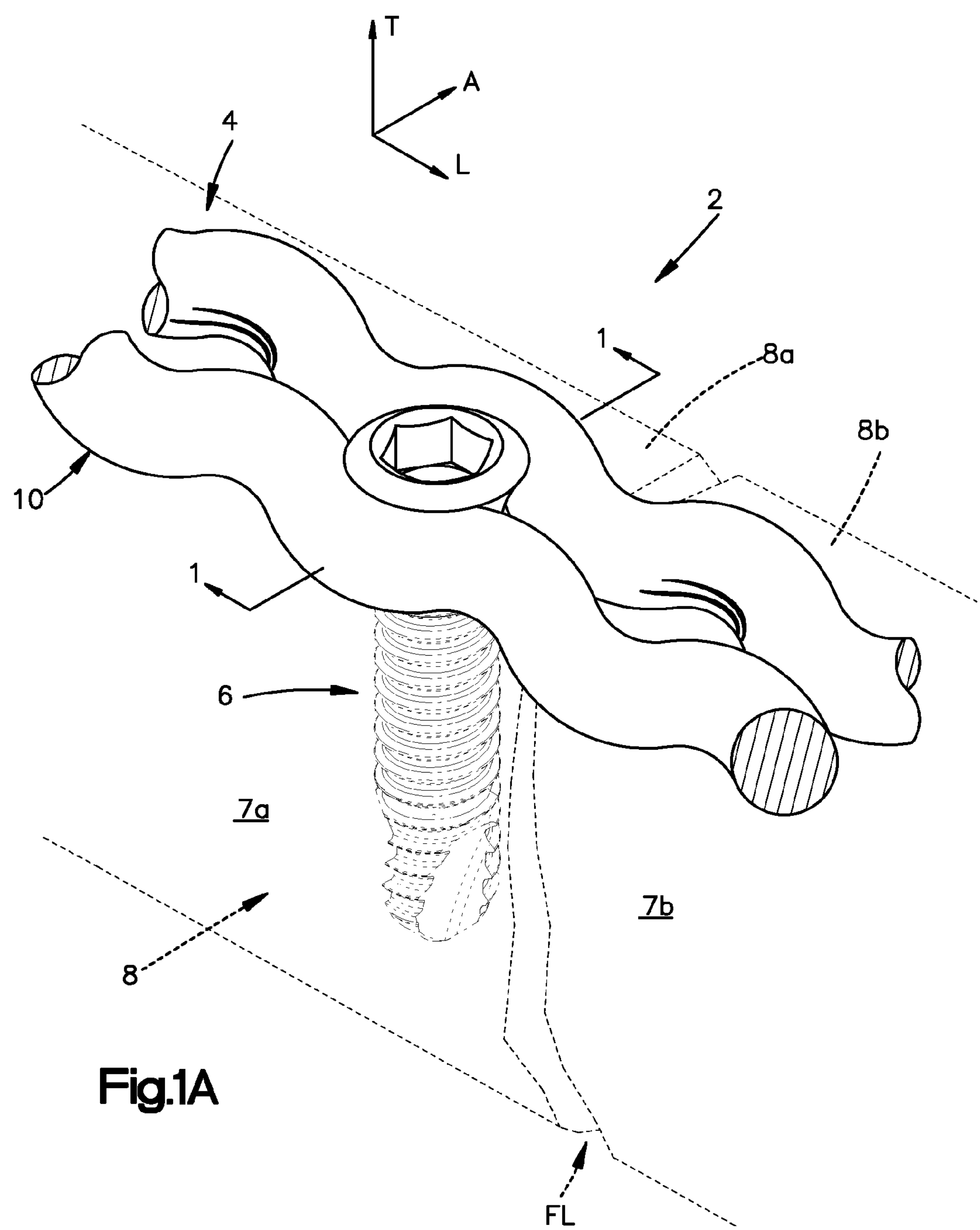
FIG. 1A is a perspective view of a bone fixation system secured to a fixation site such as a bone, according to an embodiment of the present disclosure.
Figure 1B:
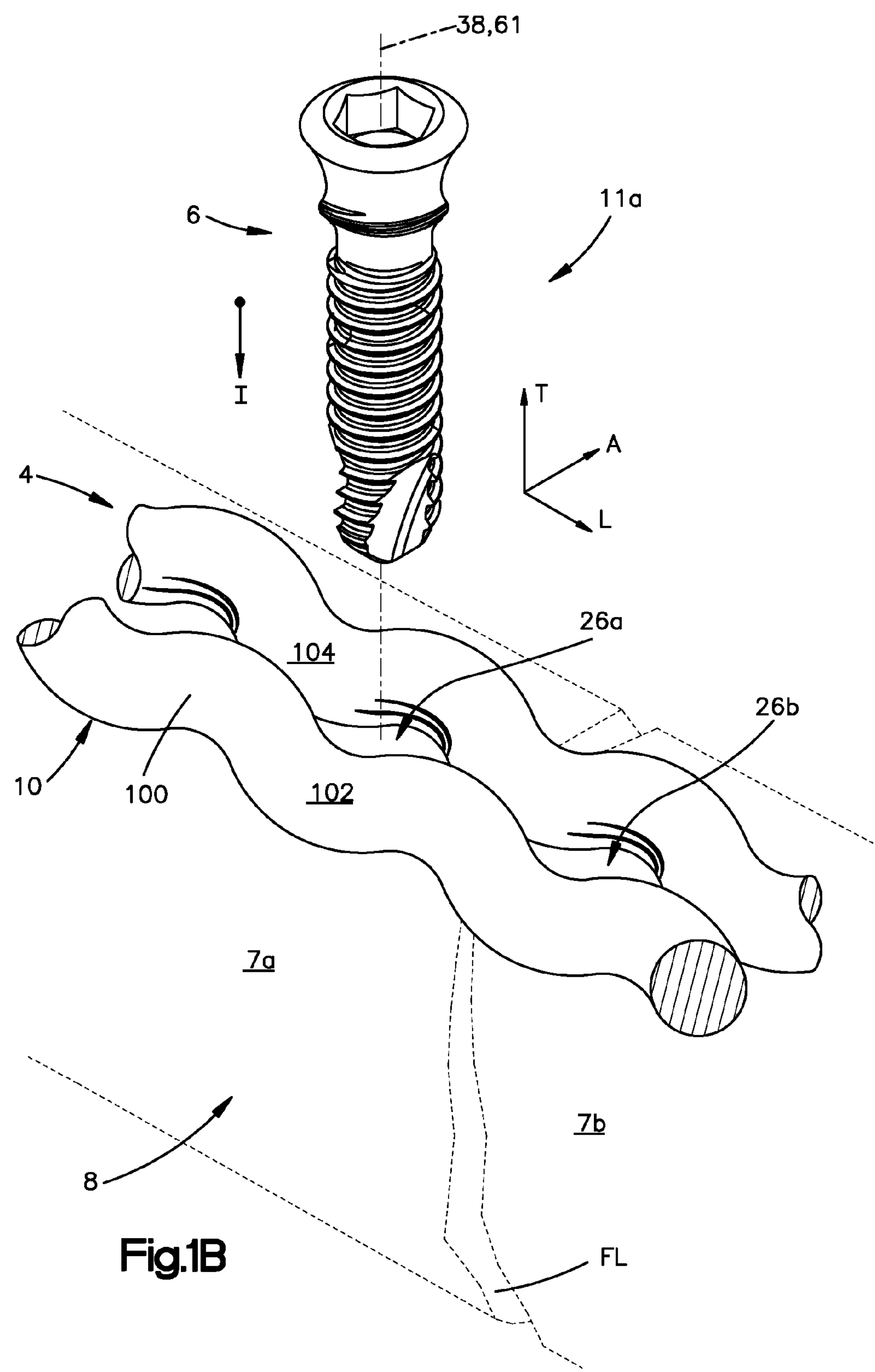
FIG. 1B is an exploded perspective view of the bone fixation system shown in FIG. 1A.
Figure 1C:
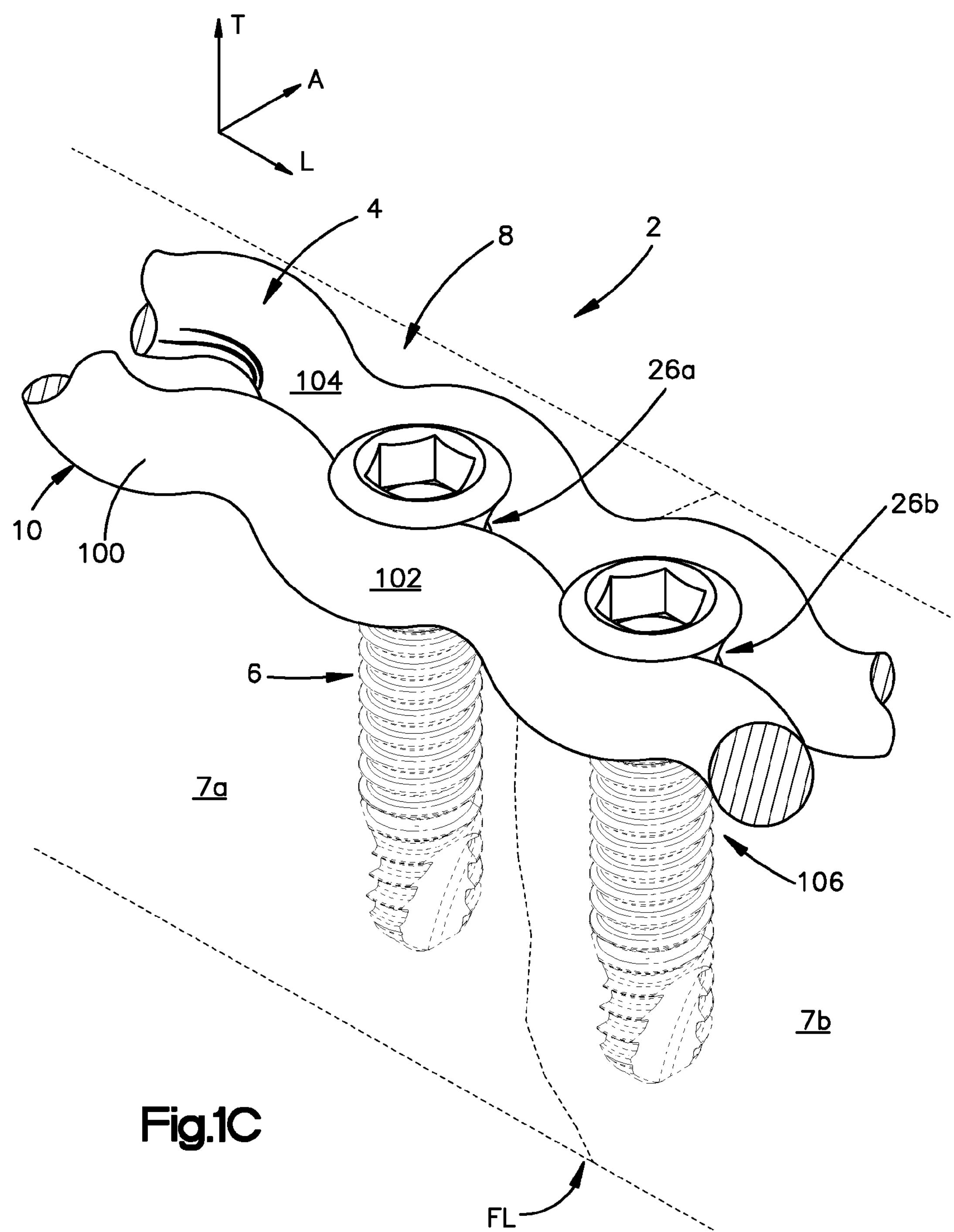
FIG. 1C is a perspective view of a bone fixation system shown in FIG. 1A, illustrating a first bone fixation element and a second bone fixation element securing a bone implant to a bone.
Figure 1D:
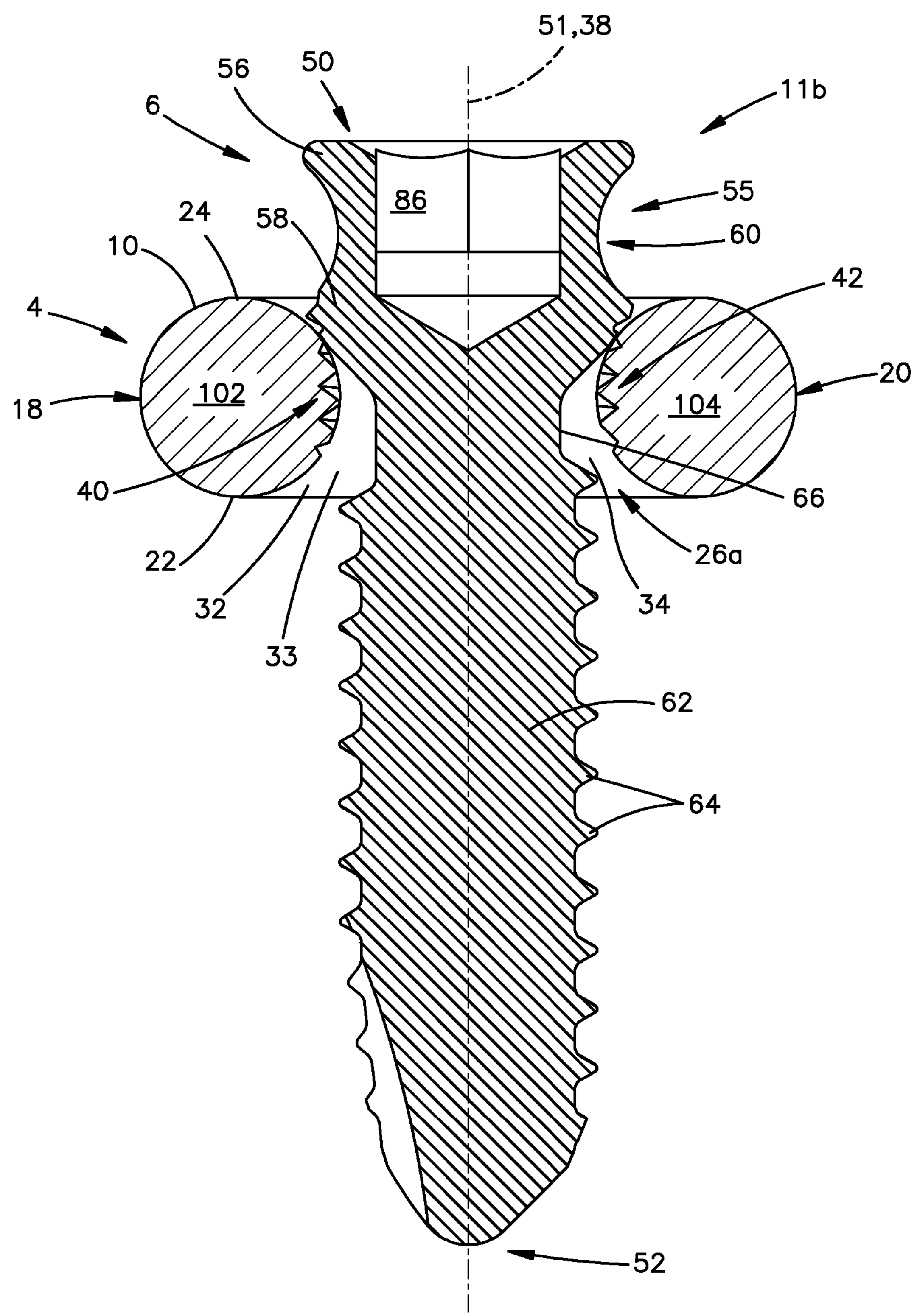
FIG. 1D is a cross-sectional view of the bone fixation system taken along line 1-1 in FIG. 1A, illustrating the bone fixation element partially inserted in the bone implant.
Figure 1E:
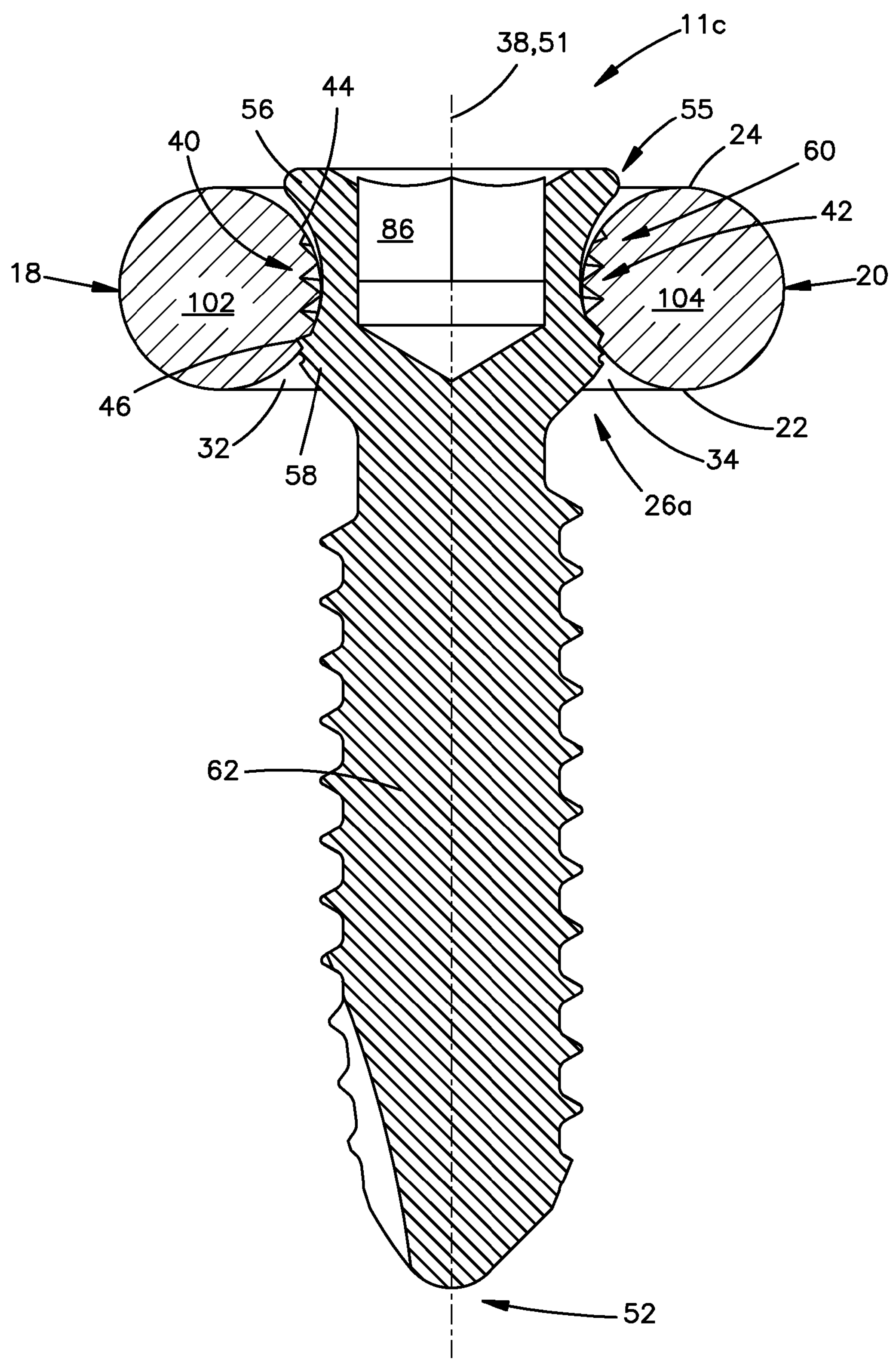
FIG. 1E is a cross-sectional view of the bone fixation system taken along line 1-1 in FIG. 1A, illustrating the bone fixation element inserted in the bone implant.

The bone fixation element 6 is coupled to the bone implant 4 when the bone fixation element 6 is fully inserted or deployed in the bone implant 4 as shown FIGS. 1A, 1C and 1E. The coupling between the bone fixation element 6 and bone implant 4 provides 1) angularly stability between the bone fixation element 6 and the bone implant 4, and 2) the ability of the bone fixation element 6 to rotate relative to the bone implant 4. For instance, when a plurality of bone fixation elements 6 are coupled to bone implant 4 and secured to the fixation site 8, angularly stable fixation is achieved because the bone implant 4 forms a stable bridging structure with the bone fixation elements 6 that spans the fracture location FL (FIG. 1C). Further, the bone fixation element 6 can be coupled to the bone implant 4 such that the bone fixation element 6 can be rotated relative to the bone implant 4. For instance, in the illustrated embodiment the bone fixation element 6 is rotatably coupled to the bone implant 4 when fully deployed or seated in the implant 4 as shown in FIG. 1E. Such rotatable coupling allows the bone fixation element 6 to rotate relative to the bone implant 4 without causing further advancement of the bone fixation element 6 along the transverse direction T through the bone implant 4. When bone fixation element 6 is coupled the bone implant 4 s and the bone fixation element 6 is secured to the fixation site 8, rotation of the bone fixation element 6 repositions the bone implant 4 closer to or further away from the fixation site 8 depending on the rotation direction of the bone fixation element 6. Accordingly, the bone implant 4 can be repositioned to a desired position relative to the fixation site 8, so that, for example, the distance between the bone implant 4 and the fixation site 8 can be set to maintain an optimal blood supply near the fixation site 8 and fracture location FL. Such coupling may also improve the tactility of insertion of the bone fixation element 6 into the fixation site 8. Bone is generally made of two types of bone, cortical and cancellous bone. The cortical bone surrounds the cancellous bone and is relatively harder than the cancellous bone. Since the bone fixation element 6 can be rotated in the bone implant 4, the user or person applying the rotation with, for example, a driving instrument, can feel during insertion when the bone fixation element 6 is advancing into relatively hard cortical bone or relatively soft cancellous bone.

Referring to FIGS. 1A and 2A-2C, the bone implant 4 defines an implant body 10 that is elongate substantially along a central implant axis 12. The bone implant 4 can extend between a first implant end 14 (not shown), and second implant end 16 (not shown) spaced from the first implant end 14 along the central implant axis 12. The first and second implant ends 14 and 16 are not shown in FIGS. 1A-1C in order to illustrate a portion of the bone implant 4. The implant body 10 includes lateral sides 18 and 20 that are spaced from each other along a lateral implant axis 13 or second direction that is perpendicular with respect to the central implant axis 12. In accordance with one embodiment, the central implant axis 12 can extend along a longitudinal direction L, and the lateral sides 18 and 20 are spaced from each other along the lateral direction A that is substantially perpendicular to the longitudinal direction L. Thus, reference to the longitudinal direction L herein refers to the central implant axis 12, unless otherwise indicated. Further, reference to the lateral direction A herein refers to the lateral implant axis 13 or the second direction, unless otherwise indicated. The implant body 10 can further define a bone facing surface 22 and an opposed or upper surface 24 that faces away from the fixation site 8 when the bone implant 4 is secured to the fixation site 8. The bone facing surface 22 and the opposed surface 24 can be spaced from each other along a transverse direction T that is substantially perpendicular with respect to both the longitudinal direction L and the lateral direction A. The bone implant 4 defines a plurality of apertures 26 that extend through the implant body 10 along the transverse direction T, and an inner wall 33 the extends along each aperture 26 between the upper surface 24 and bone-facing surface 22. The inner wall 33 can be at least partially curved along the transverse direction T.

The bone implants of present disclosure are described herein as extending horizontally along a longitudinal direction "L" and a lateral direction "A", and vertically along a transverse direction "T". Unless otherwise specified herein, the terms "longitudinal," "transverse," and "lateral" are used to describe the orthogonal directional components of various bone fixation system components and component axes. It should be appreciated that while the longitudinal and lateral directions are illustrated as extending along a horizontal plane, and that the transverse direction is illustrated as extending along a vertical plane, the planes that encompass the various directions may differ during use. Further, the description refers to bone fixation system components and/or portions of such components that include a "proximal end" and a "distal end." Thus, a "proximal direction" or "proximally" refers to a direction that is oriented generally from the distal end toward the proximal end. A "distal direction" or "distally" refers to a direction that is oriented generally from the proximal end toward the distal end.

Figure 2A:
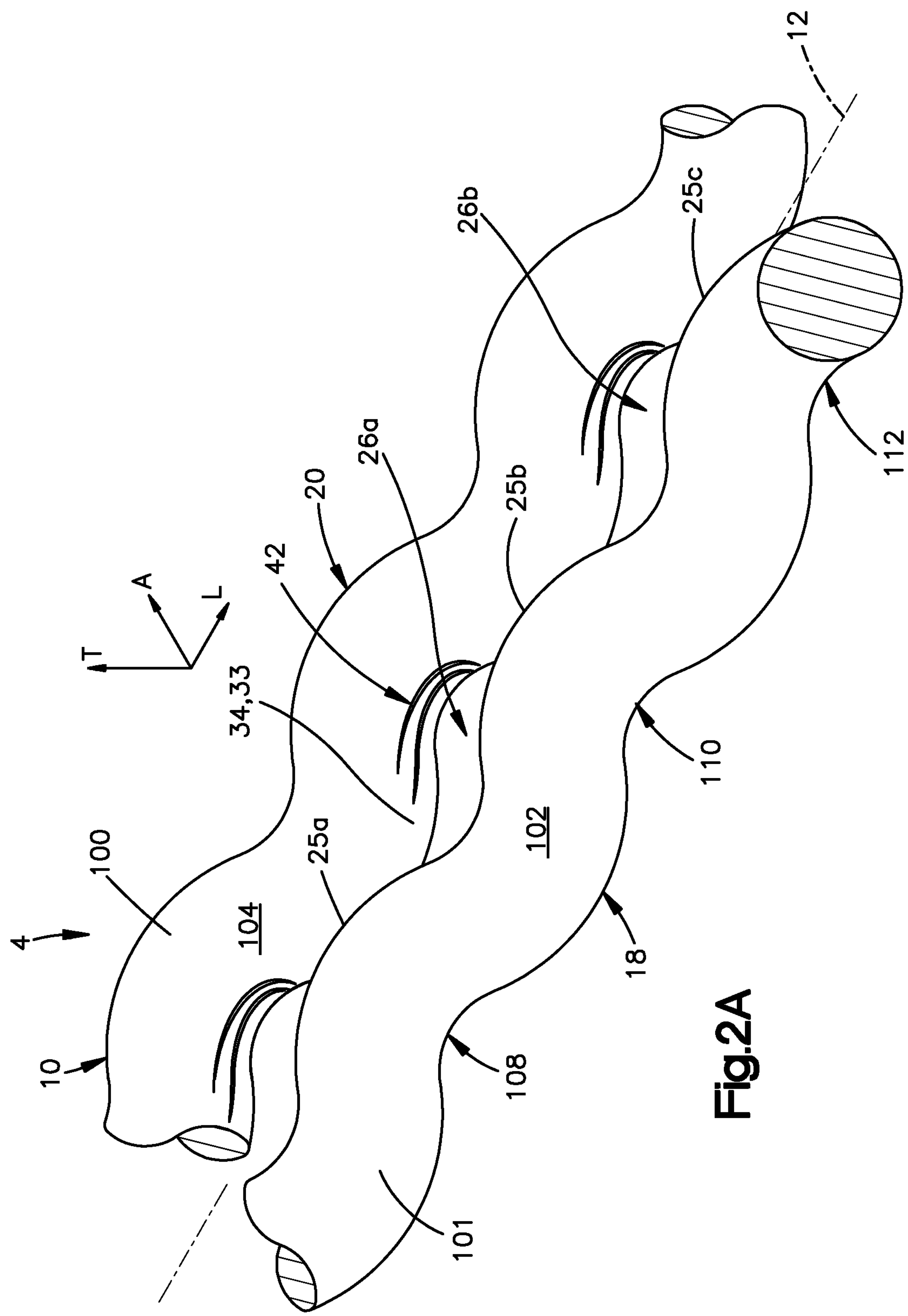
FIG. 2A is a perspective view of the bone implant shown in FIG. 1A.
Figure 2C:
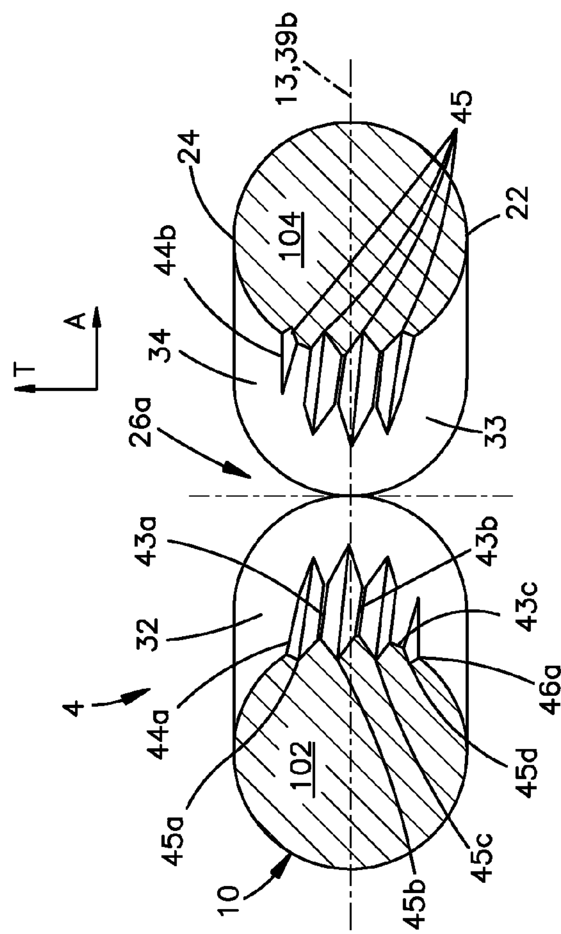
FIG. 2C is a cross-sectional view of the bone implant shown in FIG. 2B taken along line 2B-2B in FIG. 2B.
Figure 2B:
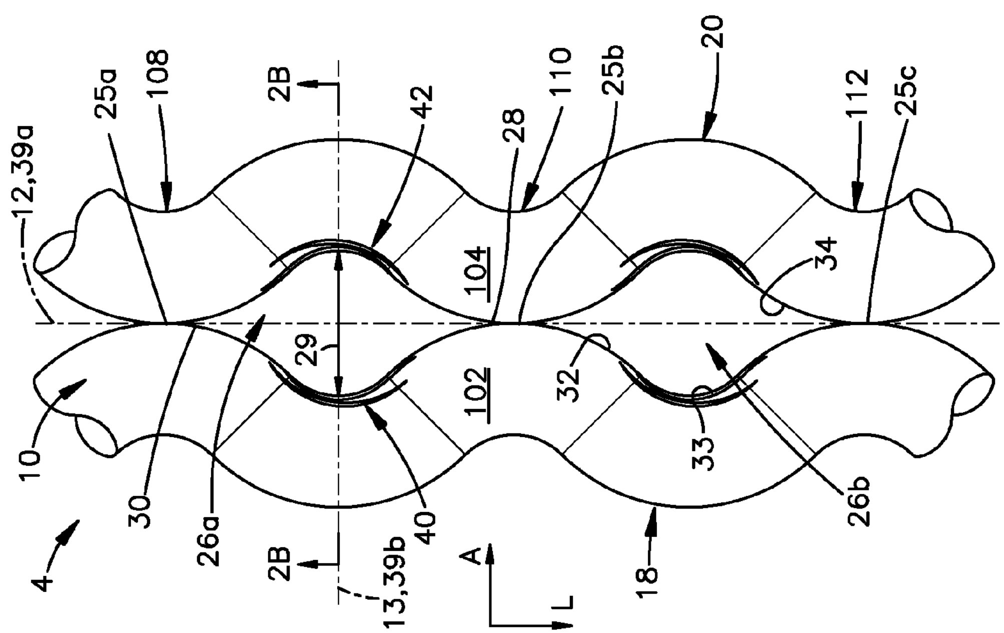
FIG. 2B is a plan view of the bone implant shown in FIG. 2A.
Figure 3A:
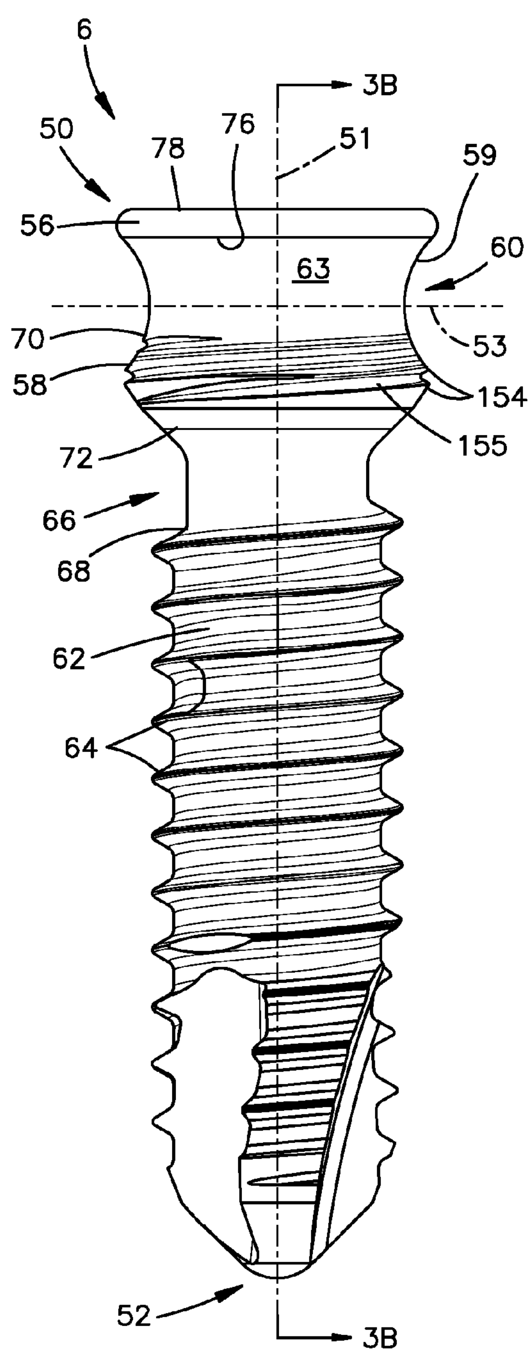
FIG. 3A is a side view of the bone fixation element shown in FIG. 1A.
Figure 3B:
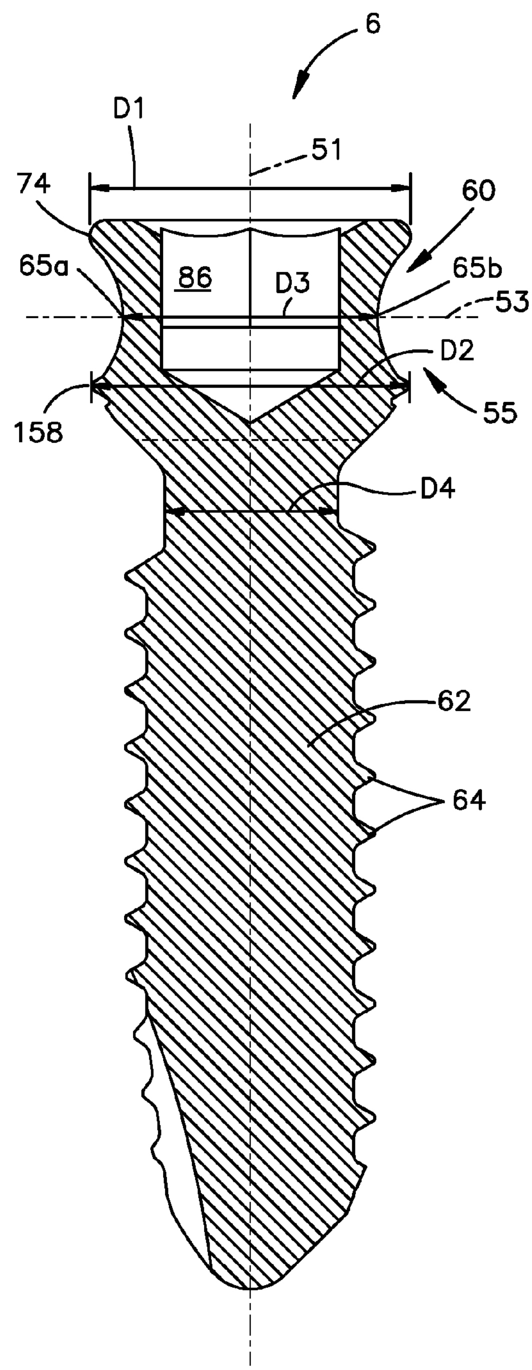
FIG. 3B is cross-sectional view of the fixation element taken along line 3B-3B in FIG. 3A.

Continuing with FIGS. 2A-2C, the bone implant 4 includes at least one wire 100 that is shaped to define the implant body 10 to define the plurality of apertures 26 that extend though implant body 10 along the transverse direction T. The bone implant 4 can be partially or completely made of wire, which can define any implant body and aperture size and shape as desired. The wire 100 can define a first wire segment 102 and a second wire segment 104 that are shaped to define the bone implant. The first and second wire segments 102 and 104 can be integral and monolithic to form the wire 100. Alternatively, the first and second wire segments 102 and 104 can be separate from each other and defined by two different respective wires. The wire 100 defines a wire outer surface 101 that includes the bone contacting surface 22, opposed surface 24, lateral sides 18 and 20, and the inner wall 33. The inner wall 33 can include a first inner wall 32 and a second inner wall 34. For instance, the wire 100 is shaped to define the inner walls 32 and 34 that define the plurality of apertures 26 as detailed below. When the wire segments 102 and 104 are formed of two wires, the two wires define different inner walls 32 and 34. When a single wire forms the wire segments 102 and 104, one wire defines the inner wall 33. As used herein, "inner wall 33" and "inner walls 33" are used interchangeably with reference to the first and second inner walls 32 and 34, unless otherwise noted. Thus, the inner wall 33 (or inner walls 32 and 34) are curved along the transverse direction T and curved along the longitudinal direction L. Portions of the inner walls 32 and 34 lie in a plane (not shown) that is perpendicular to the lateral implant axis 13 so that the bone contacting surface 22 may lie substantially flush to a bone and the opposed surface 24 faces away from the bone contacting surface 22, and thus away from the fixation site 8. While a bone implant 4 that includes a wire 100 is illustrated in FIGS. 1A-7B, the bone implant 4 can be formed of a bone plate as shown in FIG. 8A-8B and further detailed below.

Continuing with FIGS. 1C, 2A-2C, the bone implant 4 defines the plurality of apertures 26 that extend though the bone implant body 10 along the transverse direction T. For instance, the first and second inner walls 32 and 34 can define each of the plurality of apertures 26 that include a first aperture 26*a* and a second aperture 26*b* that is spaced from the first aperture 26*a* along the longitudinal direction L. The bone implant 4 can include a number of apertures as needed. The first and second apertures 26*a* and 26*b* are configured to receive bone fixation elements therein. In particular, the bone fixation element 6 can be a first bone fixation element 6 that is configured for insertion in the first aperture 26*a*. The bone fixation system 2 can also include a second bone fixation element 106 (FIG. 1C) that is configured for insertion in the second aperture 26*b* so as to secure a bone implant 4 to the fixation site 8 and fuse the first and second bone fragments 7*a* and 7*b* together.

Continuing with FIGS. 2A-2C, in the illustrated embodiment the first and second wire segments 102 and 104 define spaced apart neck portions 108, 110, 112 that at least partially define the apertures 26. The apertures 26 can be elongate along the longitudinal direction L. The neck portions 108, 110, 112 define respective intersection points 25*a*, 25*b*, 25*c* where the first inner wall 32 and second inner wall 34 abut. The first wire segment 102 extends along the longitudinal direction L between adjacent necks 108 and 110 and adjacent necks 110 and 112 to define the first inner wall 32. The second wire segment 104 extends along the longitudinal direction L between the adjacent necks 108 and 110 (and 110 and 112) to define the second inner wall 34. The first and second wire segments 102 and 104 extend along the longitudinal direction L to define spaced apart longitudinal ends 28 and 30 of the apertures 26 defined by a pair of adjacent necks. Thus, each aperture 26 extends between a first or proximal longitudinal end 28 and second or distal longitudinal end 30 spaced from the first longitudinal end 28 along the central implant axis 12 between adjacent intersection points 25.

As discussed above each aperture 26 extends along the inner walls 32 and 34 through the implant body 10 along the transverse direction T. In the illustrated embodiment, the wire 100 or wire segments 102 and 104 have a circular cross-sectional shape such that a portion of the inner walls 32 and 34 are curved with respect to the transverse direction T. The bone implant body 10 defines a central aperture axis 38 that extends along the transverse direction T, an aperture lateral axis 39*a* that extends along the lateral direction A through opposed portions of the wire segments 102 and 104, and a second or aperture longitudinal axis 39*b* that extends through opposed first and second longitudinal ends 28 and 30. The aperture longitudinal axis 39*b* is coaxial with the central implant axis 12. In other embodiments, the aperture 26 cross-section along a plane that is aligned with the central implant axis 12 can be elongate, slot-shaped, elliptical, circular or polygonal. Accordingly, the apertures 26 can be elongate along the longitudinal direction L (or elongate along the lateral direction A). When the aperture is circular, the first and second longitudinal ends 28 and 30 and the inner walls 32 and 34 define a radial extremity of the aperture 26. For circular apertures (FIG. 9), the aperture lateral axis 39*a* and the aperture longitudinal axis 39*b* are referred to as the aperture radial axis 39.

Continuing with FIGS. 2A-2C, the inner wall 33 of the implant body along the aperture 26 is at least partially threaded. In the illustrated embodiment, the first and second inner walls 32 and 34 define a pair of opposed threaded regions that threadably engage portions of the bone fixation element 6 dependent on the axial position of the bone fixation element 6 in the aperture 26. The pair of threaded regions include a first threaded region 40 and a second threaded region 42 disposed on first and second wire segments 102 and 104, respectively. Thus, the inner wall 32 defines the first threaded region 40 and the inner wall 34 defines the second threaded region 42. Each threaded region 40 and 42 extends between a proximal end 44 and a distal end 46 spaced from the proximal end 44 along the central aperture axis 38. Specifically, the first threaded region 40 extends between a proximal end 44*a* and a distal end 46*a* on the first wire segment 102, and the second threaded region 42 extends between a proximal end 44*b* and a distal end 46*b* on the second wire segment 104. Further, the first and second thread regions 40 and 42 extend longitudinally along a portion of the inner walls 32 and 34, respectively. Alternatively, the first and second threaded regions extend along the inner walls 32 and 34 between aperture ends 28 and 30 to define single threaded region disposed on each respective wall 32 and 34. In the illustrated embodiment, the first and second inner walls 32 and 34 are convex.

Each threaded region 40 and 42 define a plurality of spaced apart peaks 43*a-c* and a plurality of valleys 45*a-d*. Adjacent pairs of peaks 43 can define a valley 45. The peaks define peak points that are aligned along a curved path. For instance, the peaks are aligned along an curved path or arc defined by the outer surface 101 of the wire 100. In particular, the peak points of the first threaded region 40 lie in a convex path. The peak points on the second threaded region 42 lie in a convex path. Each valley 45 defines a valley point and each valley point can be axially aligned to define a line that is parallel to the central aperture axis 38. Alternatively, each valley point lies along a curved path or line.

Continuing with reference to FIGS. 2A-2C, the upper surface 24 and the bone-facing surface 22 can be curved or linear. A portion of the upper surface 24 extending from the proximal ends 44 of each threaded region 40 and 42 toward the lateral sides 18 and 20 is curved or convex. Further, the portion of the bone-contacting surface 22 that extends from the distal ends 46 of each threaded region 40 and 42 toward the lateral sides 18 and 20 is curved or convex. While the peaks of the threaded regions lie along a convex path as shown in FIGS. 1A-2C, in alternative embodiments the peaks of threaded regions 40 and 42 can lie along a curved path that has a curvature that is different from the curvature of the upper surface 24 and the bone-facing surface 22. Further, one or more of the peaks of the threaded regions 40 and 42 may lie along a path that is linear (FIGS. 4A-6B and 9).

Referring to FIGS. 1D, 1E and 3A-3B, the bone fixation element 6 has a proximal end 50, a distal end 52 spaced from the proximal end 50 along an element axis 51 in a distal direction. The central axis 51 is coaxial with the central aperture axis 38 when the bone fixation element 6 is disposed in the aperture 26 (FIG. 1E). The bone fixation element 6 can also define a radial axis 53 that is perpendicular to the central axis 51. The bone fixation element 6 can also threadably engage a bone. The bone fixation element 6 can be an anchor, rivet, bone pin or screw configured for securement to the fixation site 8. The illustrated bone fixation element 6 is a self-tapping screw. However, the skilled person would understand that the fixation element 6 could be a screw, for example a standard screw, that is a non self-tapping screw or a self-drilling screw.

The bone fixation element 6 can define a fixation body 54 extending between the proximal end 50 and the distal end 52. The bone fixation body 54 has a head 55 disposed at the proximal end 50 and a shaft 62 that extends distally with respect to head 55. The head 55 defines a first ridge 56, a second ridge 58 that is spaced distally from the first ridge 56 along the central axis 51, and an groove 60 between the first ridge 56 and the second ridge 58. The groove 60 is configured to receive a portion of the inner wall 33 of the bone implant 4 to secure the bone fixation element 6 to the bone implant 4. The groove 60 is recessed into the head 55 toward the central axis 51 between the first and second ridges 56 and 58. In an the illustrated embodiment, the groove 60 is unthreaded. The bone fixation body 54 defines a proximal surface 78 that is transverse to the central axis 51. The head 55 extends from the proximal surface 78 to a head distal end 72 that is spaced from the proximal surface 78 along the central axis 51. The head 55 also defines an outer head surface 59 that defines the outer extremity of the head 55. The proximal surface 78 further defines a socket 86 that extends into the bone fixation body 54 along the central axis 51 toward the distal end 52 of the bone fixation element 6. The socket 86 can have any suitable shape to receive a tool, such as a driving instrument. For instance, the socket 86 can be a square, hex, cross, slot, flat, star, hexalobular, or any other suitable shape to receive a tool. Further, the bone fixation body 54 can be cannualated (not shown) from the socket 86 to the distal end 52 and may include one or more transverse bores extending through the body 54 to the cannulation. The transverse bores are configured for receiving additional fixation elements therethrough, such as a temporary guidewire or Kirschner wire, or an additional screw that can be inserted through the socket 86 and the transverse bore to secure to a bone or an implant. The transverse bores can also allow for bone ingrowth as well. The fixation body 54 also defines a neck 66 disposed between the head 55 and the shaft 62. The shaft 62 includes threads 64 for threadably engaging the fixation site 8. The shaft threaded portion can extend from the neck 66 distally to the distal end 52 of the bone fixation element 6.

The first ridge 56 is configured to engage a portion of the bone implant 4. The first ridge 56 can be generally convex with respect to the central axis 51 so that the first ridge extends outwardly from the central axis 51. Further, the first ridge 56 is circumferentially disposed around the head 55 along a line (not shown) that is perpendicular to the central axis 51. The first ridge 56 extends from the proximal surface 78 to a first ridge distal end 76 that is spaced distally from the proximal surface 78 along the central axis 51. The head 55 can define a first ridge apex or first apex 74 disposed at the outer head surface 59 between the proximal surface 78 and the first ridge distal end 76. The ridge distal end 76 can mate with or abut the inner walls 32 and 34 of the bone implant 4 when the bone fixation element 6 is inserted in the aperture 26. The first ridge 56 defines a first ridge cross-sectional dimension D1 defined as the distance between diametrically opposed points of the first apex 74. The first cross-sectional dimension D1 can range between about 1 mm and about 15 mm. In an exemplary embodiment, D1 can be about 3.5 mm. When the bone fixation element 6 is fully inserted through the aperture 26, the head proximal surface 78 and a portion of the upper surface 24 lie on similar a plane (not shown) that is parallel to the central implant axis 12. In alternative embodiments, at least a portion of the first ridge 56 can be linear. Other ridge configurations are possible as described below with respect to FIGS. 9A-9J.

The second ridge 58 is configured to threadably engage portions of the bone implant 4 depending on the axial position of the bone fixation element 6 in the aperture 26. The second ridge 58 can be generally convex with respect to the central axis 51 so that the second ridge extends outwardly from the central axis 51. The second ridge 58 is circumferentially disposed around the head 55 along a line (not shown) that is perpendicular to the central axis 51. The second ridge 58 extends between a second ridge proximal end 70 and the head distal end 72 that is spaced distally from the ridge proximal end 70 along the central axis 51. The head 55 defines a second ridge apex or second apex 158 that is disposed between the proximal end 70 and head distal end 72. The second apex 158 can be equidistant between the second ridge proximal end 70 and the head distal end 72. The second apex 158 can also be axially aligned with the first apex 74 of first ridge 56. In alternative embodiments, at least a portion of the second ridge 58 can be linear between the second ridge proximal end 70 and the head distal end 72 to define a ridge face (not shown) that protrudes radially outward with respect to the central axis 51. The second ridge 58 defines a second cross-sectional dimension D2 that extends between the most radially outward points shown at apex 158. The second or ridge cross-sectional dimension D2 can range between about 1 and about 15 mm. In an exemplary embodiment, D2 can be about 3.5 mm. As illustrated, the second cross-sectional dimension D2 is no greater than the first cross-sectional dimension D1 of the first ridge 56. In an exemplary embodiment, D1 and D2 are the same. However, as the skilled person would of course understand, the second cross-sectional dimension D2 can be less than or greater than the first cross-sectional dimension D1 of the first ridge 56.

The head 55 is threaded at a location between the groove 60 and the shaft 62 so that the threads of the head 55 can threadably engage the threaded inner wall 33 of the bone implant 4. In one embodiment, the second ridge 58 is at least partially threaded to engage with the threaded regions 40 and 42 as the bone fixation element 6 is advanced through the aperture 26. For instance, the second ridge 58 can include a thread with one or more thread peaks 154*a-c*. Adjacent thread peaks define valleys 155 *a-c*. The peaks 154 are aligned along an arc defined by the head outer surface 59. In the illustrated embodiment, thread peak 154*b* defines the ridge apex 158. The second ridge 58 can be entirely threaded as shown, or partially threaded. When the bone fixation element 6 is fully inserted in the aperture 26 as shown in FIG. 1E the second ridge 58 threadably disengages from the pair of threaded regions 40 and 42. When the thread second ridge 58 disengages, the a portion of the inner wall of the bone implant 4 is held or seated between the first ridge 56 and the second ridge 58. Because the bone implant 4 held between the first ridge 56 and the second ridge 58 angularly stable fixation is achieved.

Continuing with FIGS. 2A and 2B, the groove 60 is configured to receive a portion of the bone implant 4. The head 55, or head outer surface 59, defines a groove surface 63 that extends between the first ridge 56 and the second ridge 58. A portion of the inner wall 33 can be received by the groove 60 between the first and second ridges 56 and 58. For instance, the groove 60 also extends from the first ridge distal end 76 to the second ridge proximal end 70 along the central axis 51, and circumferentially around the bone fixation body 54 with respect to the central axis 51. The groove 60 can define a third or groove cross-sectional dimension D3. The groove cross-sectional dimension is defined as the distance between opposing points 65 *a-b* located on the groove surface 63 lying on a plane that is perpendicular to the central axis 51 and spaced equidistant between the first apex 74 and second apex 158. While the groove cross-sectional dimension D3 can vary as needed, the groove cross-sectional dimension D3 is no greater than either or both of the first cross-sectional dimension D1 and the second cross-sectional dimension D2. For example, D3 can be 3.0 mm when the D1 and/or D3 is 3.5 mm as discussed above. However, it should be appreciated that D3 can vary from 3.0 mm. As discussed above, the groove 60 conforms to the curved inner walls 32 and 34 such that the groove 60 abuts the threaded regions 40 and 42 when the bone fixation element 6 is inserted in the aperture 26. In the illustrated embodiment, the groove surface 63 is concave and conforms to the convex inner walls 32 and 34 as well as portions of the upper surface 24 and bone-facing surface 22. In an exemplary embodiment, the concavity of the groove surface 63 has a radius of curvature that matches the radius of curvature of the inner walls 32 and 34, or matches the curvature of the wire or a portion of the bone implant 4.

Figure 5B:
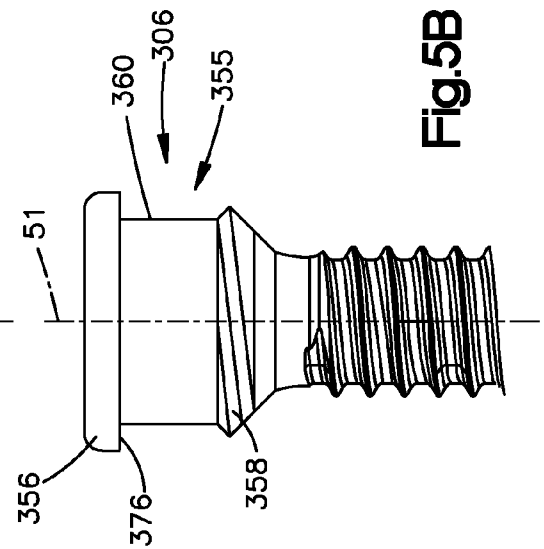
FIG. 5B is a bone fixation element configured for the bone implant shown in FIG. 5A.
Figure 5A:
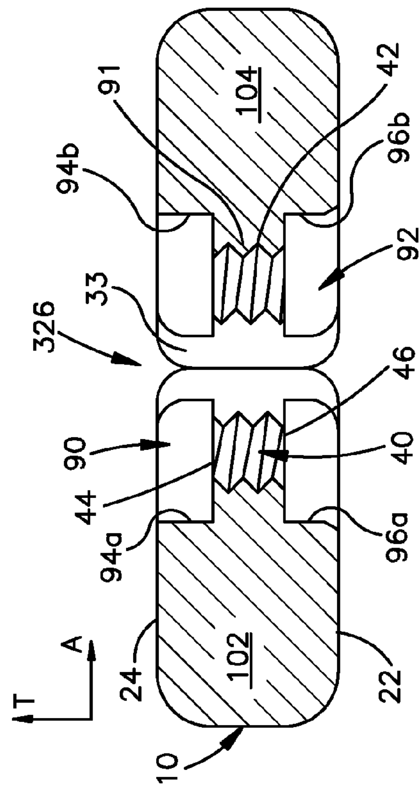
FIG. 5A is a sectional view of a bone implant according to an alternative embodiment of the present disclosure.
Figure 6B:
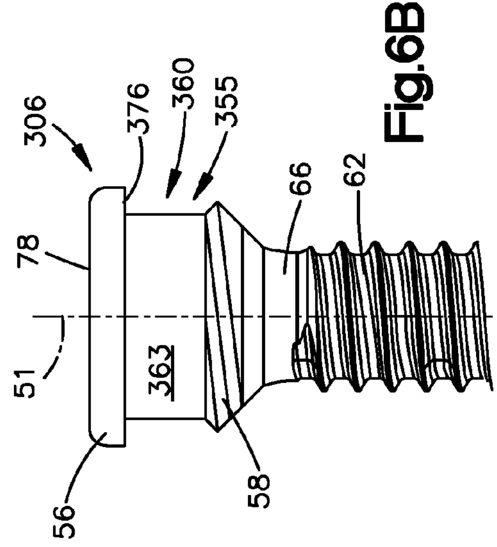
FIG. 6B is a fixation element configured for the bone implant shown in FIG. 6A.

In alternative embodiments, at least a portion of the groove 60 is linear such that a portion of the groove surface 63 is parallel to the central axis 51 (FIGS. 5B and 6B) offset with respect to the first ridge 56 and second ridge 58 along the radial axis 53 (FIGS. 5A and 5B). Further, the groove surface 63 can be tapered proximally from the second ridge 58 toward the first ridge 56 such that the groove 60 has a cross-sectional dimension that is narrow near the first ridge 56 and larger near the second ridge 58. Alternatively, the groove surface 63 can be tapered distally from the first ridge 56 toward the second ridge 58 such that the groove 60 has a cross-sectional dimension that is narrow near the second ridge 58 and larger near the first ridge 56.

To achieve coupling between the bone fixation element 6 and the bone implant 4, the bone fixation element 6 is configured so that the groove 60 and inner walls 32 and 34 fit snuggly together with minimal or no gap. The aperture 26 can have an aperture dimension 29 (FIG. 2B) that is defined as the distance between opposing points located in each threaded region 40 and 42 lying on a similar plane that extends through the inner walls 32 and 34 along radial axis 53. The aperture cross-sectional dimension 29 can range between 1-mm or and 15 mm as needed. However, the aperture cross-sectional dimension 29 can be greater than 15 mm as needed when the apertures are configured as elongate slots.

Continuing with reference to FIGS. 1A to 1E, the neck 66 is disposed between the head 55 and shaft 62. The neck 66 extends between the head distal end 72 and the proximal end 68 of the shaft 62. In the illustrated embodiment, the neck 66 is concave and extends toward the central axis 51. A distal portion of the head 55 and the proximal end 68 of the shaft 62 define an angle $\alpha$. Angle $\alpha$ can range between 45 degrees and 75 degrees. In one embodiment, an angle $\alpha$ is about 60 degrees. The neck 66 can define a neck or fourth cross-sectional dimension D4 defined as the distance between opposed radial points (not shown) of the shaft 62. The fourth cross-sectional dimension D4 is less than one or both the first cross-sectional dimension D1 and the second cross-sectional dimension D2 . The fourth cross-sectional dimension D4 can range between 0.5 and 14.5 mm. In an exemplary embodiment, D4 can be about 1.6 mm when D1 and D2 are about 3.5 mm. The neck 66 is configured to ease insertion of the head or second ridge 58 of the bone fixation element 6 into the aperture 26.

Figure 4B:
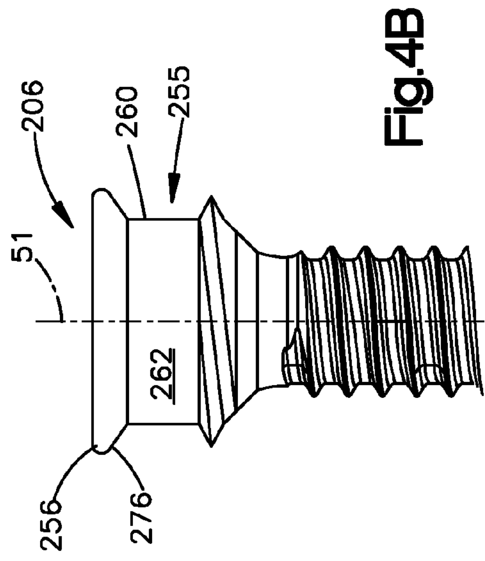
FIG. 4B is a bone fixation element configured for the bone implant shown in FIG. 4A.
Figure 4A:
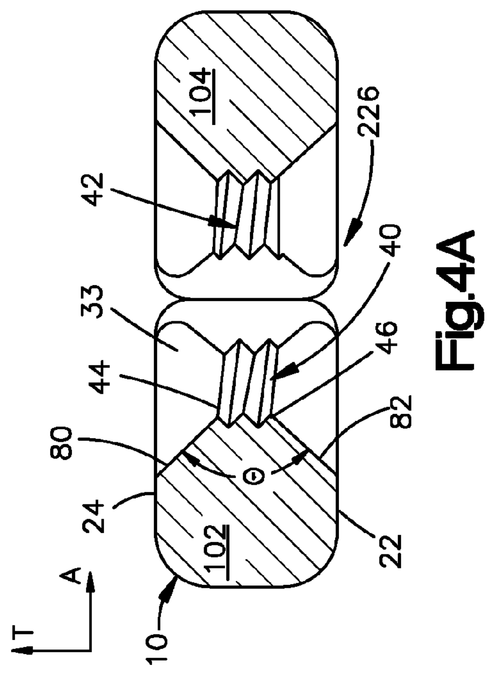
FIG. 4A is a sectional view of a bone implant according to an alternative embodiment of the present disclosure.

Referring to FIGS. 4A-7B, in accordance with alternative embodiment, the bone fixation systems include a bone implant 4 that defines an implant body 10. The implant body 10 includes wire segments 102 and 104 that include neck portions 108, 110, 112 with intersection points 25. The implant body 10 also defines an inner wall 33 extending along the aperture 226. The inner wall 33 defines a pair of spaced apart threaded regions 40 and 42. At least a portion of the upper surface 24 extends from the proximal end 44 of each threaded regions 40 and 42 along the lateral direction A. A portion of the bone-contacting surface 22 also extends from the distal end 46 of each threaded region 40 and 42 along the lateral direction A as discussed above. Further, the bone fixation elements shown in FIGS. 4B, 5B, 6B and 7B, include a head, a shaft and a neck. The head defines a first ridge, a second ridge, and a groove. In accordance with the alternative embodiments, the wire 100 can have different cross-sectional shapes, such as rectangular, square or elliptical shapes. Thus, the wire 100 can define aperture profiles 226, 326 and 426 as shown in FIGS. 4A, 5A, and 7A.

Turning to FIG. 4A, in accordance with the alternate embodiment, the implant body 10 defines an aperture 226 extending through the implant body 10. The inner wall 33 includes a first inclined portion 80 that extends from the proximal ends 44 of threaded regions 40 and 42 to the upper surface 24. The inner wall 33 can include a second inclined portion 82 that extends from the distal ends 46 of threaded region 40 and 42 to the bone-facing surface 22. The first inclined portion 80 and the second inclined portion 82 define an angle $\theta$ therebetween. Angle $\theta$ can be a right angle or an oblique angle as needed. Referring to FIG. 4B, the bone fixation element 206 includes head 255 defining a first ridge 256, a second ridge 258, and a groove 260 between the first and second ridges 256 and 258 that is configured to receive the inner wall 33. In accordance with an alternate embodiment, the first ridge 256 defines a distal face 276 that is angularly offset with respect to central axis 51 and forms a portion of the groove 260. The groove surface 262 is linear along a central axis 51 from the distal face to the second ridge 258. The distal face 276 conforms to first inclined portion 80 when the bone fixation element 6 is inserted into the aperture 226.

Turning to FIGS. 5A-6B, in accordance with an alternative embodiment, the implant body 10 defines an inner wall 33 and an aperture 326 that extends along the inner wall 33 and through the implant body 10. The inner wall 33 defines a first recess 90 disposed proximally in the aperture 326, projections 91 distal to the first recess 90 and protruding into the aperture 326 along the lateral direction A, and a second recess 92 disposed distal to the projections 91 in the aperture 326. The threaded regions 40 and 42 are disposed at the projection 91. The implant body 10 can also define a first set of vertical faces 94*a* and 94*b* that extend from the projection 91 to the upper surface 24 along the transverse direction T. The first set of vertical faces 94*a* and 94*b* and a portion of the projections 91 define the first recess 90. The implant body 10 also defines a second set of vertical faces 96*a* and 96*b* that extend distally from the projections 91 to the bone-facing surface 22 along the transverse direction T. The second set of vertical faces 96*a* and 96*b* and a portion of the projections 91 define the second recess 92. In accordance with an alternative embodiment as shown in FIG. 5B, the bone fixation element 306 includes a head 355 that defines a first ridge 356, a second ridge 358, and a groove 360 that is configured to mate with the profile of inner wall 33 of the bone implant 4 shown in FIGS. 5A and 6A. The first ridge 356 includes a distal face 376 that is transverse to the central axis 51. In particular, the first ridge 356 can fit within the first recess 90, the groove 360 receives the threaded regions 40 and 42, and the second ridge 358 at least partially fits within the second recess 92. When the bone fixation element 6 is inserted in the aperture 326, the first ridge 356 fits within the first recess 90 so that the distal face 376 abuts the projections 91 and vertical faces 94*a* and 94*b*.

Figure 7B:
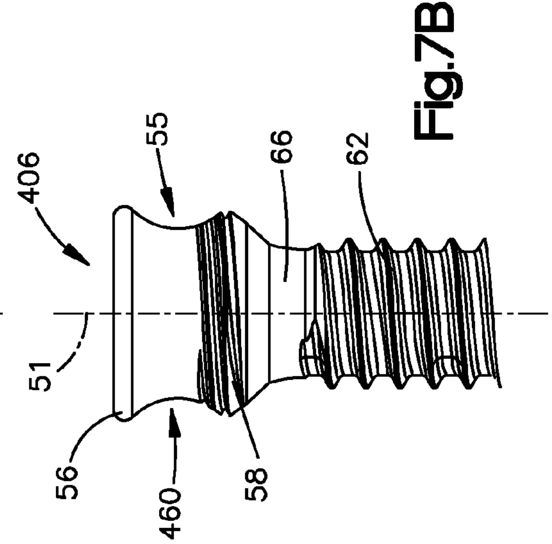
FIG. 7B is a bone fixation element configured for the bone implant shown in FIG. 7A.
Figure 6A:
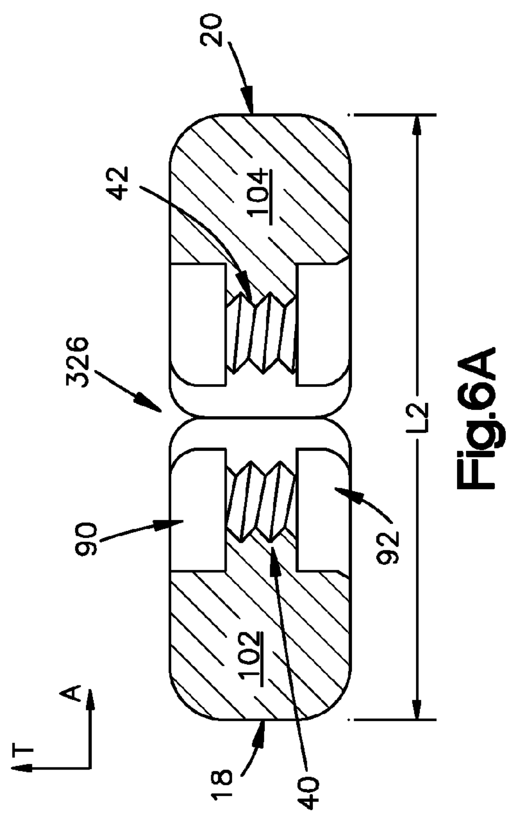
FIG. 6A is a sectional view of a bone implant according to an alternative embodiment of the present disclosure.
Figure 7A:
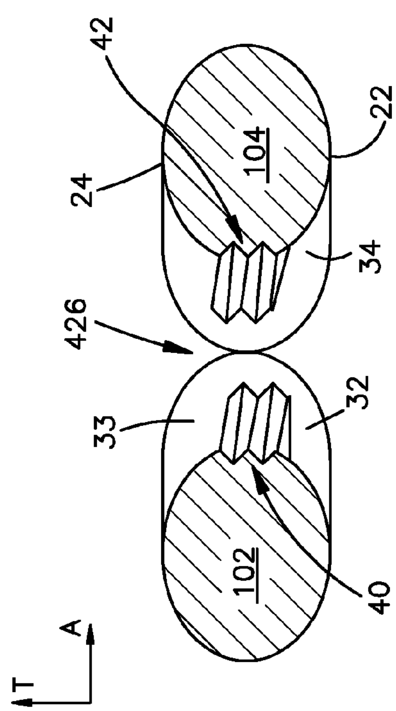
FIG. 7A is a sectional view of a bone implant according to an alternative embodiment of the present disclosure.
Figure 8A:
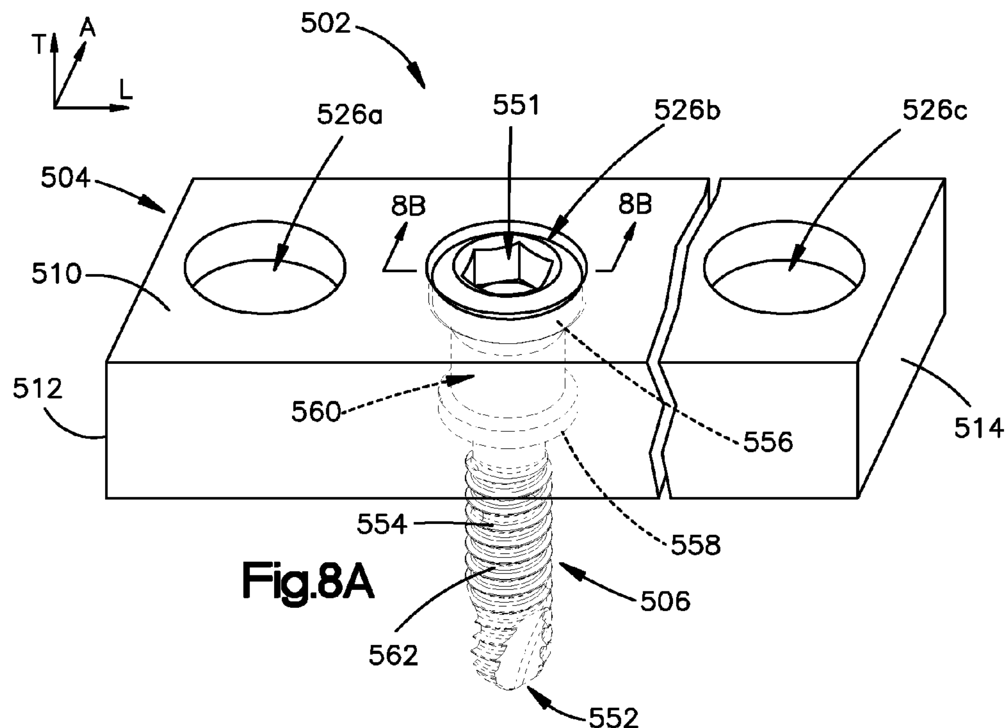
FIG. 8A is a perspective view of a bone fixation system according to an alternative embodiment of the present disclosure.
Figure 8B:
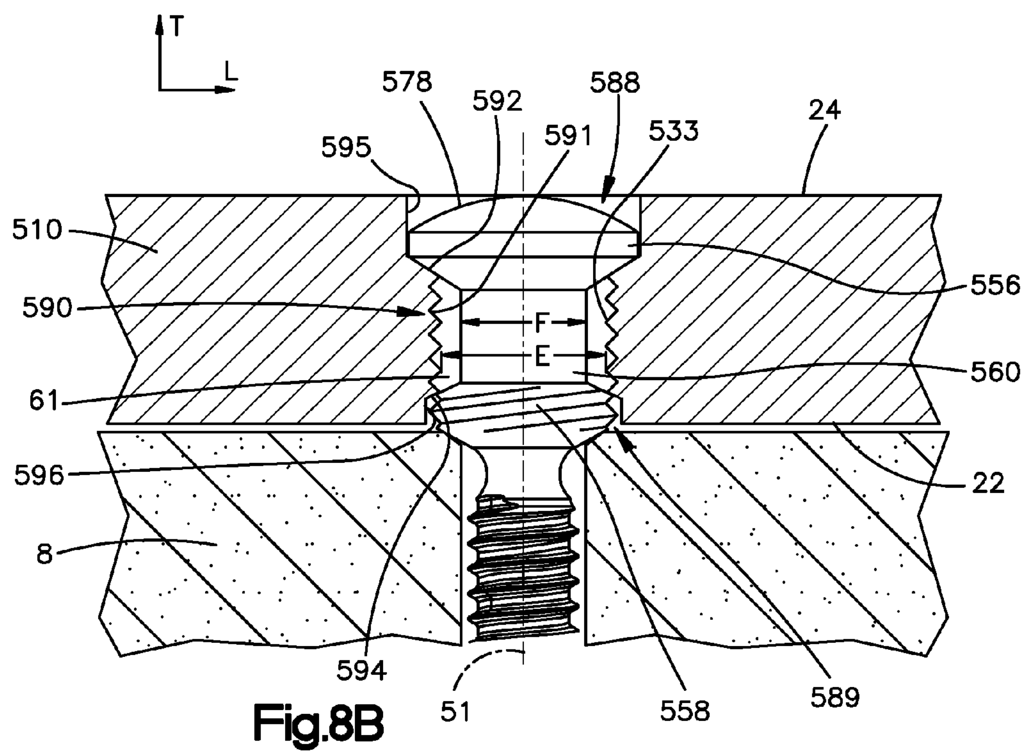
FIG. 8B is a cross-sectional view of the bone fixation system taken along line 8B-8B in FIG. 8A.

Referring to FIGS. 7A-7B, the bone fixation system 404 includes a bone implant 404. The bone implant 404 includes the implant body 10 with wire segments 102 and 104 having elliptical cross-sectional shapes. The bone fixation element 406 has a groove 460 that is concave and has a curvature that conforms to curvature of the inner wall 33 defined by the elliptically shaped wire segments of the implant body 10.

Referring again to FIGS. 1A-1E, in accordance with another embodiment, a method for coupling the bone fixation element 6 to the bone implant 4 can include advancing the bone fixation element 6 through multiple axial positions in the aperture 26. In the illustrated embodiment the positions can include 1) a first or insertion position 11*a* as shown in FIG. 1B), 2) a second or initial engagement position 11*b* as shown in FIG. 1D), and 3) a third deployed or seated position 11*c* as shown in FIGS. 1A and 1E.

When the bone fixation element 6 is in the insertion position 11*a*, the bone fixation element 6 is aligned with the aperture 26. The bone fixation element 6 is shown aligned with the central aperture axis 38. Next, the bone fixation element 6 is advanced through the aperture 26 along an insertion direction I so that that the shaft 62 passes through the aperture 26. The insertion direction I is aligned with the central axis 51 of the bone fixation element 6. A tool (not shown) can engage the socket 86 and cause rotation of the bone fixation element 6 about the central axis 51 so that the shaft 62 threadably engages the fixation site 8. Further advancement of the bone fixation element 6 along the insertion direction I causes the threaded second ridge 58 to threadably engage the threaded regions 40 and 42 at the initial engagement position 11*b* shown in FIG. 1D. Still further advancement of the head 55 through aperture 26 causes the bone implant 4 to seat in the groove 60 so that the groove 60 receives the inner walls 32 and 34 of the bone implant 4. That is, rotation of the bone fixation element 6 advances the second ridge 58 along the threaded regions 40 and 42 in the insertion direction I until the second ridge 58 threadably disengages from the threaded regions 40 and 42 (FIG. 1E). When the bone fixation element 6 is in the deployed position 11*c*, the first ridge 56 and the second ridge 58 moveably couple the bone implant 4 to the bone fixation element 6. For instance, the bone fixation element 6 can be further rotated so as to reposition the bone implant 4 along the transverse direction T relative to the fixation site 8. Thus, rotation of the bone fixation element in a first rotational direction (not shown) can reposition the bone implant 4 closer to the fixation site 8. Rotation of the bone fixation element 6 along second rotation direction (not shown) that is opposite to the first rotational direction can reposition the bone implant 4 further away from the fixation site 8. Accordingly, the distance between the bone implant 4 and the fixation site 8 can be adjusted when the bone fixation element 6 is coupled to the bone implant 4. Further, when the bone implant 4 includes elongate apertures, the bone implant 4 can be reposition relative to the fixation site along a lateral direction and/or longitudinal direction L. That is, the bone implant 4 can reposition so that the bone fixation element 6 translated along the inner walls of the aperture 26 until the bone implant 4 is in desired position.

Referring to FIG. 1C, in accordance with an alternate embodiment, the method can included coupling an additional bone fixation element to the bone implant 4. For instance, the bone fixation system can include the second bone fixation element 106. The second bone fixation element 106 can be inserted through the second aperture 26*b* so that the groove 160 (not shown) receives the bone implant 4 in a manner similar to how the first bone fixation element 6 is inserted in the first aperture 26*a* described above. While the first and second bone fixation elements 6 and 106 can be configured similarly as described in the present disclosure, the first and second bone fixation elements can be different types of bone fixation elements. For instance, the bone fixation element 6 can be configured as described herein to moveably couple with the bone implant 4, and the second bone fixation element 106 can be a conventional locking screw, non-locking screw, a compression screw, variable angle screw, or another other type of bone fixation element.

Referring to FIG. 8A, the bone fixation system 502 can include a bone implant 504 and a bone fixation element 506 configured to couple with the bone implant 504. The bone implant 504 can include a bone plate body 510. In the embodiment illustrated in FIGS. 8A and 8B, the plate body 510 can be a monolithic plate body or comprises multiple plate segments. The plate body 510 can extend between an upper surface 524 and a bone-facing surface 522 spaced from the upper surface 524 along the transverse direction T. The plate body 510 can define an inner wall 533 that further defines the aperture 526 that extends through the plate body 510 along the transverse direction T. The inner wall 533 is at least partially threaded to engage with the bone fixation element as described above. The bone implant 504 defines a central aperture axis 38 (not shown). The inner wall 533 defines a first recess 588 positioned proximally in aperture 526 toward the upper surface 524, a protrusion 590 distal to the first recess 588, and a second recess 589 disposed distal to the protrusion 590 in the aperture 526. The protrusion 590 extends into the aperture 526 along a lateral direction A to define a protrusion face 591. The protrusion 590 also extends along the transverse direction T between a protrusion proximal face 592 and a protrusion distal face 594. The proximal and distal faces 592 and 594 can be inclined or curved. In the illustrated embodiment, the protrusion face 591 is threaded similar to the threaded regions 40 and 42 discussed above. However, portions of the recesses can be threaded as well. Further, the protrusion can include a pair of opposed threaded regions that are circumferentially spaced from each other on the inner wall 533. Alternatively, the protrusion can 590 can define a single threaded region. The inner wall 533 also defines a first vertical face 595 that extends from the proximal face 592 of the protrusion 590 and is parallel to the aperture axis 538. The vertical face 595 and proximal face 592 define the first recess. The inner wall 533 also define a second vertical face 596 that is parallel to the aperture axis 538 and extends from the distal face 594 of the protrusion 590 to the bone-facing surface 522. The second vertical face 596 and distal face 594 of the protrusion 590 define the second recess 588. The aperture 526 has a cross-sectional dimension E, which is the distance between a pair of opposed points (not shown) located on the protrusion terminal end 591.

Continuing with FIG. 8B, the bone fixation element 506 includes fixation body 554 having a head 555 and shaft 562 extending distally with respect to the head 555. The head 555 includes a first ridge 556, a threaded second ridge 556 and a groove 560 extending between the first ridge 556 and the threaded second ridge 556. The first ridge 556 is configured to be received by the first recess 588 of the plate body 510, the groove 560 is configured to conform to or receive the protrusion 590, and the second ridge 556 is configured to be disposed at least partially in the second recess 589 of the plate body 510. The groove 560 defines a cross-sectional dimension F, which is the distance between a pair of opposed points located on the outer surface 563 of the groove 560. The bone fixation system 502 is configured so that the groove cross-sectional dimension F is less than the aperture cross-sectional dimension E. That is, a gap 61 extends between the groove 560 and the protrusion terminal end 591. The gap 61 permits the bone fixation element 506 with respect to the bone implant 504. The aperture cross-sectional dimension E can be greater than the groove cross-sectional dimension D3 to define a gap distance G (not shown). The gap distance G can be 0(zero) or near 0(zero) when the groove 560 is configured to abut the inner walls 32 and 34, or greater than 0 (zero) when the groove 560 and inner walls 32 and 34 define the gap 61. In one embodiment, the gap distance G can be up to about 0.3 mm. Thus, the gap 61 can be constant along the groove surface 563. However, the gap 61 can also vary depending on the configuration of the groove 560. For instance, the gap 61 near the first ridge 556 can be larger than the gap 61 near the second ridge 558 when the groove 560 is tapered proximally from the second ridge 558 toward the first ridge 556. Alternatively, the gap 61 can be larger near the second ridge 558 compared to the gap 61 near the first ridge 556 when the groove 560 is tapered distally from the first ridge 556 toward the second ridge 558.

In accordance with an alternative embodiment, the head 555 of the bone fixation element 506 can include threads at location between the groove 560 and the shaft 562 that can threadably engage the threaded protrusions 590 when the bone fixation element is advancing through the aperture 526. As the groove 560 advances through the aperture 526, the threads on the head 555 threadably disengage from the threaded protrusion 590.

While the bone fixation element 506 is illustrated coupled to the bone plate body 510, the bone fixation element 506 is configured for coupling to the bone implant 4 described above and shown in FIGS. 1A-7B. Further, the bone fixation element 6 as described above is configured for coupling to the bone plate body 510 shown in FIGS. 8A and 8B.

Referring to FIGS. 9A-9J, in accordance with alternative embodiments of the present disclosure, various embodiments of a bone fixation element are illustrated in the deployed position in the bone implant 4. The bone implants 4 include an implant body 10 having wire segments 102 and 104 that define apertures as discussed above. The implant body 10 shown in FIG. 9A-9J can also include a bone plate that defines apertures as described and shown in FIGS. 8A and 8B. Specifically, any of the bone fixation elements illustrated in FIGS. 9A-9J can be coupled to any of the bone implants 4 and 504 described above and shown in FIGS. 1A-8B. Accordingly, the bone fixation elements can include a head 55, a shaft 62, and a neck 66 between the head 55 and the shaft 62, as described above. The head 55 includes a first ridge 56, a groove 60 having a groove surface 63, and a second ridge 58. The implant body 10 can include the curved inner wall 33.

Figure 9A:
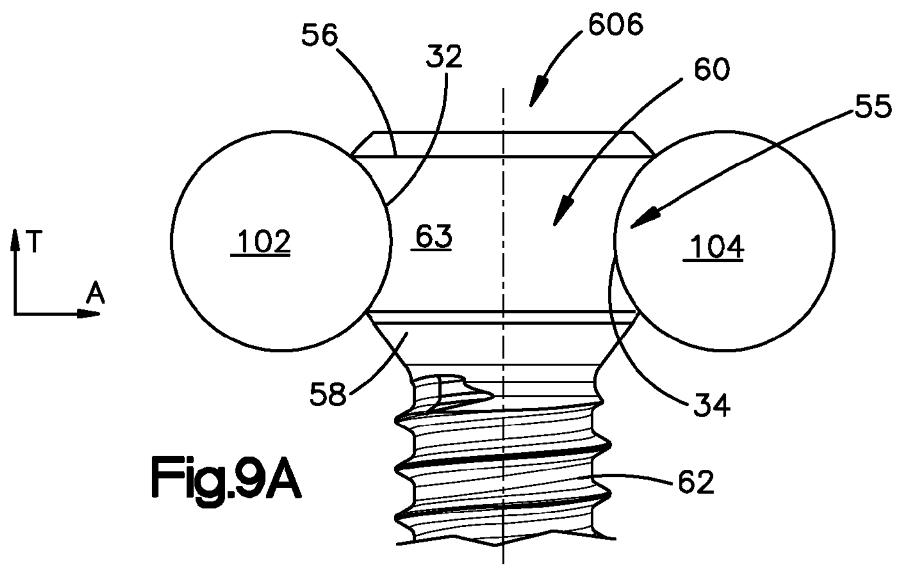
FIGS. 9A-9J are sectional views of bone fixation systems according to other alternative embodiments of the present disclosure.

Referring to FIG. 9A, in accordance with an alternative embodiment, the bone fixation element 606 includes a groove 60 that is concave and conforms with a portion of the wire segments 102 and 104. The first ridge 56 and second ridge 58 can have similar cross-sectional dimensions. The inner wall 33 (not shown) is unthreaded and the head 55 is unthreaded.

Figure 9B:
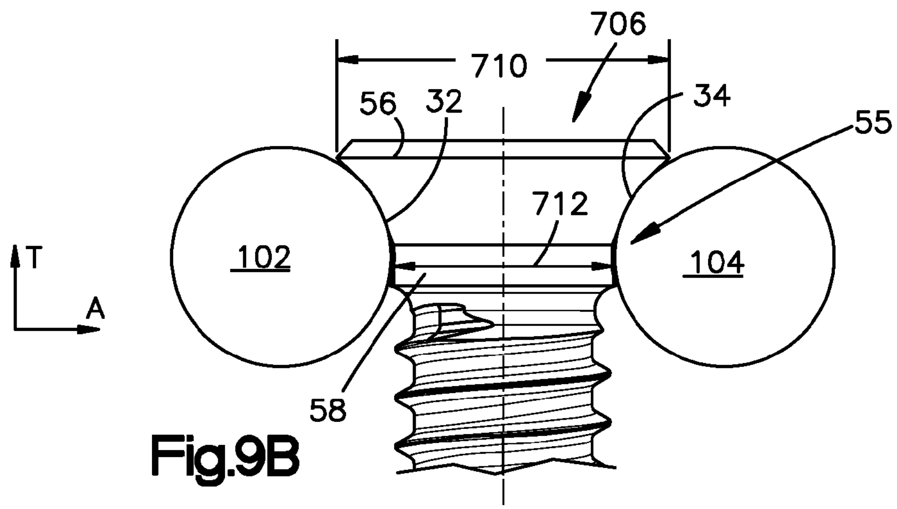

Referring to FIG. 9B, the bone fixation element 706 includes a head 55 with a tapered groove 60. The first ridge 56 has a first cross-sectional dimension 710 that is greater than a second cross-sectional dimension 712 of the second ridge 58. Thus, the groove 60 is distally tapered from the first ridge 56 toward the second ridge 58. The groove 60 receives the inner wall 33 and extends over a portion of the upper surface 24 along the lateral direction A toward opposing sides 18 and 20 (not shown). Further, the head 55 of the bone fixation element 706 is unthreaded and the inner wall (not shown) of the bone implant 4 is unthreaded.

Figure 9C:
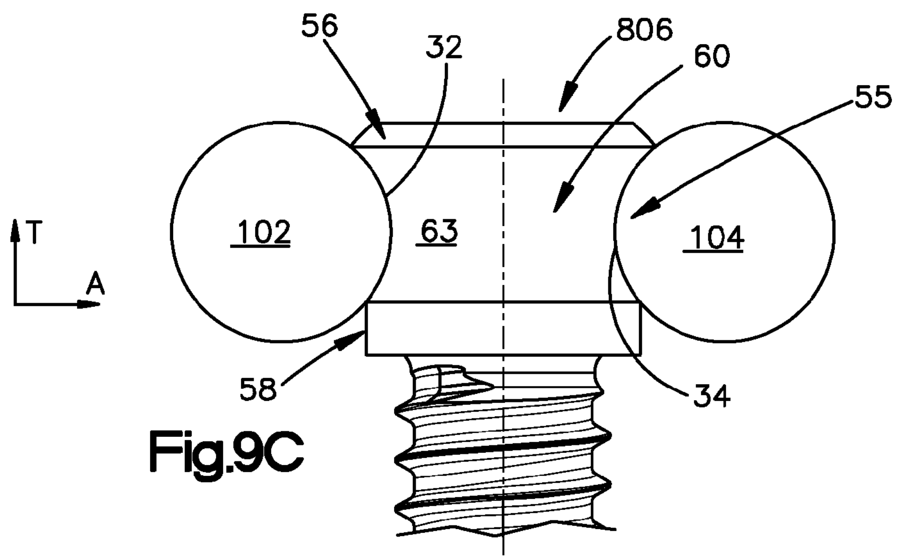

In FIG. 9C, the bone fixation element 806 includes a first ridge 56 and second ridge 58 is configured so that the groove 60 extends over at least a majority of inner walls 32 and 34. The implant body 10 can be resiliently flexible. In particular, the wire 100 is flexible so that the first and second wire segments 102 and 104 can be flexed or biased to facilitate insertion of the bone fixation element 6 through the aperture 26. Thus, the implant body 10 can be flexed or biased from an initial unbiased configuration as shown in FIG. 9C to a biased or flexed position (not shown) where the wire segments 102 and 104 separate along the lateral direction A so as to increase the size and dimension of the aperture 26. The second ridge 58 extends from distal end 864 of the groove surface a distal face 859 and projects outwardly with respect to the neck 66. The second ridge 58 can be used to help bias the wire segments 102 and 104 apart during insertion of the fixation element 806 through the aperture.

Figure 9D:
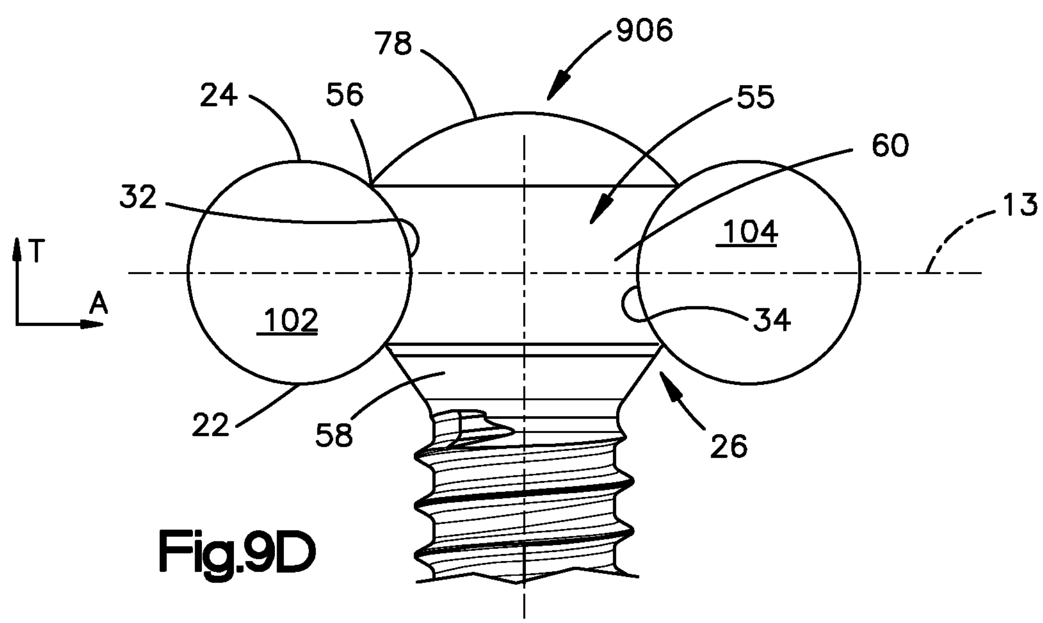

Turning to FIGS. 9D, the bone fixation element 906 includes a proximal surface 78. The bone fixation element 906 is configured so that when the bone fixation element 906 is fully inserted through the aperture 26, a portion of the proximal surface 78 protrudes through a plane P (not shown) that is parallel to the lateral implant axis 13 and contains an upper most portion of the upper surface 24. Further, as shown in FIG. 9D, the groove 60 receives the inner walls 32 and 34 and extends over a portion of the upper surface 24.

Figure 9E:
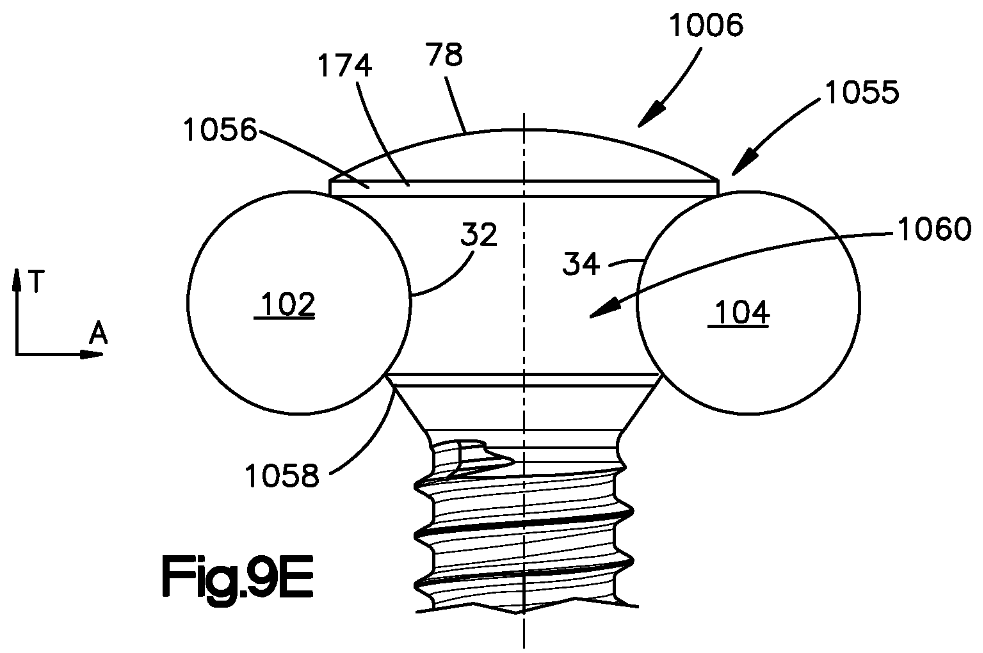

In FIG. 9E, the head 55 of the bone fixation element 1006 includes a first ridge 1056 that defines a lip 174 that extends along the inner walls 32 and 34 and the upper surface 24. The ridge 1056 can apply a force to the implant body 10 along the transverse direction T toward the fixation site 8.

Figure 9F:
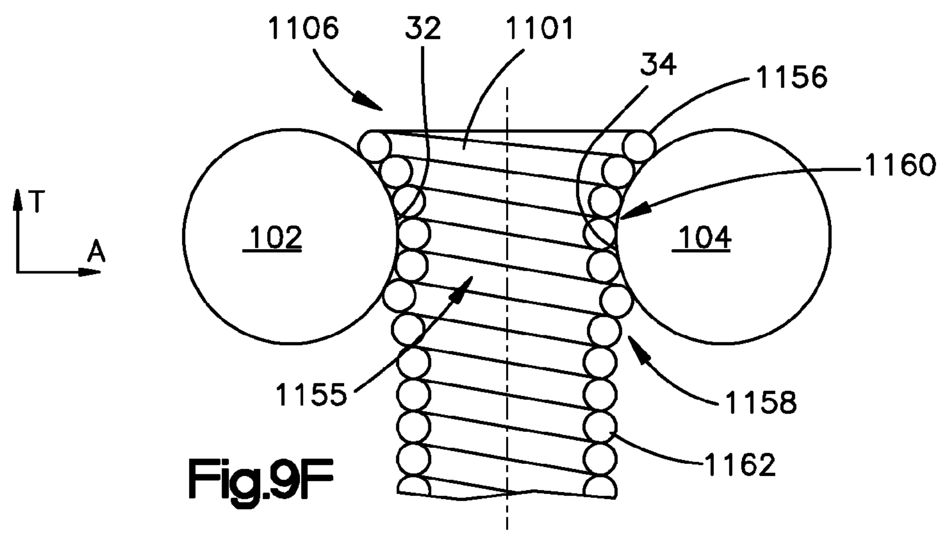

Referring to FIG. 9F, the bone fixation element 1106 can be formed of at least one wire 1101. The wire 1101 can be coiled so as to define a bone fixation body 1154 that includes a head 1155 and shaft 1162 extending distally form the head 1155. The head 1155 can also include a first ridge 1156, second ridge 1158, and a groove 1160 disposed between the first and second ridges 1156 and 1158. One or more wires segments can define the first ridge 1156, the second ridge 1158, and the groove 1160.

Figure 9G:
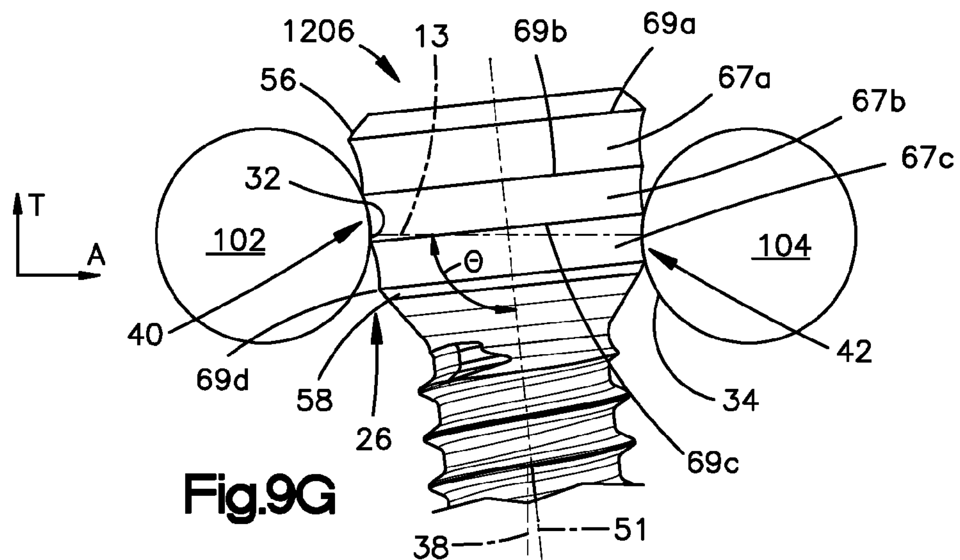

Turning to FIG. 9G, the bone fixation element 1206 is configured as a variable angle bone fixation element. For instance, the fixation body 54 defines a groove 1260 that extends between the first ridge 56 and the second ridge 58. The groove 1260 includes a plurality of groove segments 67 *a-c*. For instance, the fixation body 54 can include a first groove segment 67*a* adjacent to the first ridge 56, a second groove segment 67*b* distal to the first groove segment 67*a*, and third groove segment 67*c* distal to the second groove segment 67*b* and adjacent to second ridge 58. While three groove segments are shown, groove 1260 can include two groove segments or more than three groove segments. The groove 1260 is circumferentially disposed around the fixation body 54, and aligned along a plane that is transverse or perpendicular to the central axis 51. Thus, each groove segment 67*a-c* is circumferentially disposed around the fixation body 54 and aligned along a plane that is transverse or perpendicular to the central axis 51. Each groove segment 67*a-c* extends between adjacent apex points 69*a-d*. The head 55 extends from the proximal surface 78 to apex point 69*d*. As discussed above, the aperture 26 includes a central aperture axis 38. The inner walls 32 and 34 include threaded regions 40 and 42 (not shown). The bone fixation element 1206 can be inserted through the aperture 26 such that the a portion of the second groove segment 67*b* is engaged with or coupled to the threaded region 40 and the spaced apart third groove segment 67*c* is engaged with or coupled to the opposing threaded region 42. The threaded regions 40 and 42 are disposed along or on a similar plane, however, the spacing between the second groove segment 67*b* and the third groove segment 67*c* are such that the central axis 51 is offset from the central aperture axis 38 at an angle θ. Angle θ is an angle defined by the central axis 51 and the implant body lateral and/or central implant axes 12. Angle θ can be a right angle, for instance when the second groove segment 67*b* is engaged with both threaded regions 40 and 42. Further angle θ can be oblique as shown in FIG. 9G.

Figure 9H:
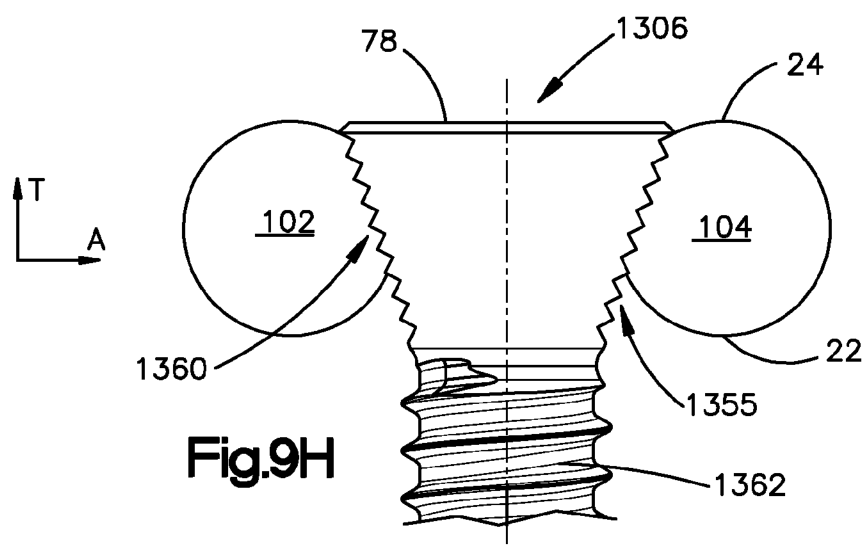
Figure 9I:
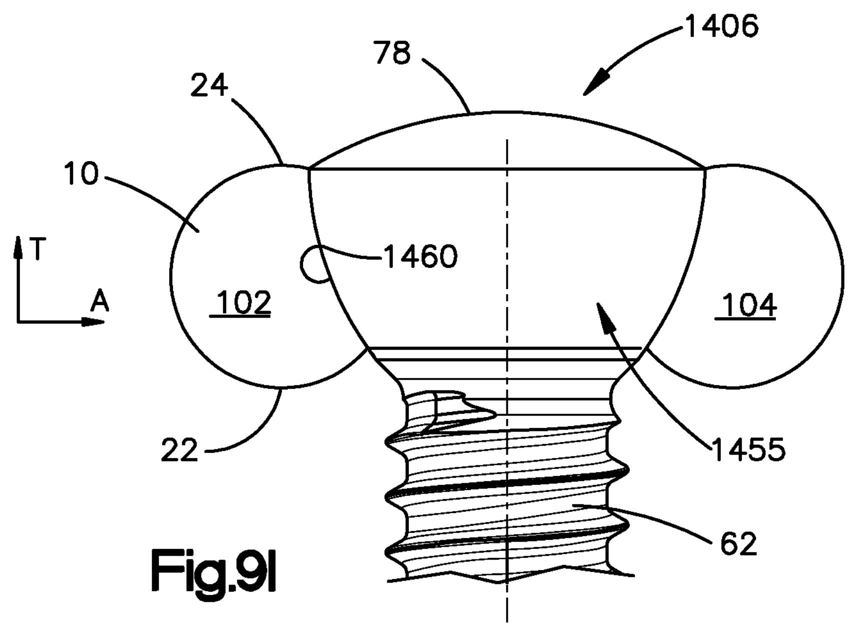

Referring to FIGS. 9H and 9I, the bone fixation system 2 can include a bone fixation element configured as a locking screw 1306 as shown in FIG. 9H, or a compression screw 1406 as shown in FIG. 9I. The locking screw head 1355 includes threaded region 1360 that tapers linearly toward the shaft 62. The threaded region 1360 threadably engages with the threaded regions 40 and 42 (not shown) of the implant body 10 in the aperture. The head 1355 defines a proximal surface 78 that is generally aligned with the upper surface 24 of the bone implant 4 when the locking screw 1306 is deployed in the aperture 26 and secured to the fixation site 8. Referring to FIG. 9I, the compression screw 1406 can include a head 1455 disposed proximally with respect to the shaft 62. The head 1455 is convex and includes threads to engage with the wire segments 102 and 104 of the implant body 10.

Figure 9J:
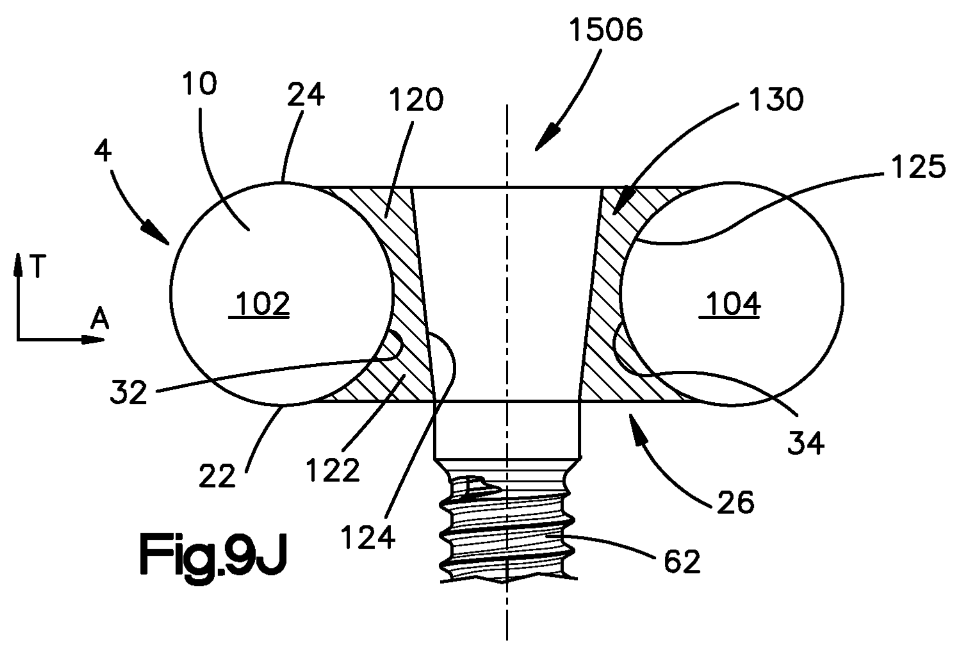

As shown in FIG. 9J, the bone fixation system 2 includes bone implant 4, and bone fixation element 1506 and a clip member 120 disposed in the aperture 26 between the bone fixation element 1506 and the bone implant 4. The bone fixation element 1306 is configured so that upon insertion into the aperture 26 the fixation body 54 is spaced from the implant body 10 to define a gap 130 extending therebetween. The clip member 120 is configured to span the gap 130 between the bone fixation element 6 and the implant body 10. The bone implant body 10 can define an aperture 26 as described above that includes an upper surface 24, threaded regions 40 and 42, and bone-facing surface 22 that are curved, or convex as shown. The clip member 120 can define an annular shaped clip body 122 having a bore 124 extending through the clip body 122 along the transverse direction T. The bore is sized and dimensioned to receive the head 55 of the bone fixation element 1506 therein. The clip body 122 defines an outer surface 125 that is concave and conforms to the convex shaped aperture 26.

Another embodiment of the present disclosure is a surgical kit including a plurality of bone implants 4, and a plurality of bone fixation elements 6 configured to couple with the bone implants 4. The kit can include one or more bone implants 4 that include a wire as described above, and one or more bone implants that include a plate. The plurality of bone fixation elements can include one or more bone fixation element 6 as described above, locking screw, compression screw, variable angle screw, or any of type of bone fixation element. The kit may also include a drill and a drill guide. The drill guide (not shown) may have a threaded end configured for insertion into the apertures of the bone implant 4, so that a drill (not shown) can be use to pre-drill a hole into which the bone fixation elements 6 can inserted.

The bone fixation system can be formed using any suitable biocompatible materials or combination of the materials. For instance, the bone implant 4 and plates 510 can be formed of metallic materials such as cobalt chromium molybdenum (CoCrMo), stainless steel, titanium, titanium alloys, magnesium, glass metals, ceramic materials, and polymeric materials include plastics, fiber reinforced plastics, polymeric materials that include polyetheretherketone (PEEK), polyetherketoneketone (PEKK), and bioresorbable materials or shape memory materials. In one embodiment, the bone implants can be formed of a combination of polymeric and metallic materials. For instance, the bone implant 4 can be formed of polymeric wires, metallic wires, or a combination of polymeric and metallic wires. The bone implants 4 and 504 may be coated an antibacterial coating, drug-eluting coating, or surface modifier such as a carbon diamond coating. In another example, the bone implants 4 and 504 may be chemically processed using, for example, anodization, electropolishing, chemical vapor deposition, plasma treatments, or any process to modify or enhance bone implant surface characteristics. The bone fixation elements can also be formed of formed of metallic materials such as cobalt chromium molybdenum (CoCrMo), stainless steel, titanium, titanium alloys, nitinol and Gummetal®, magnesium, glass metals, ceramic materials, and polymeric materials include plastics, fiber reinforced plastics, polymeric materials that include polyetheretherketone (PEEK), polyetherketoneketone (PEKK), and bioresorbable materials or shape memory materials. The bone fixation elements can also be metallic or formed of metallic alloys, such as titanium. The bone fixation element can also be formed of a combination of polymeric and metallic materials. For instance, the bone fixation element can have a polymeric head and metallic shaft. The bone fixation elements may be coated an antibacterial coating, drug-eluting coating, or surface modifier such as a carbon diamond coating. In another example, the bone fixation elements may be chemically processed using, for example, anodization, electropolishing, chemical vapor deposition, plasma treatments, or any process to modify or enhance bone fixation element surface characteristics Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the processes, machines, manufacture, composition of matter, means, methods, or steps, presently existing or later to be developed that perform substantially the same function or achieve substantially the same result as the corresponding embodiments described herein that may be utilized according to the present disclosure.

What is claimed:

1. A bone fixation system comprising:

a bone implant elongate along a longitudinal direction, the bone implant including an implant body that defines an upper surface, a bone-facing surface spaced from the upper surface along a transverse direction that is perpendicular to the longitudinal direction, at least one aperture that extends through the implant body along the transverse direction, the at least one aperture defined by an inner wall, wherein the inner wall is defined by a first and a second wire segment, and a portion of the inner wall is curved along the transverse direction to define a convexly shaped outer surface, and wherein the inner wall comprises a first threaded region on the convexly shaped outer surface; and at least one bone fixation element configured to be inserted at least partially through the at least one aperture into an underlying bone, the bone fixation element defining a proximal end and a distal end spaced from the proximal end along a central axis in a distal direction, the bone fixation element defining a head disposed at the proximal end and a shaft that extends relative to the head towards the distal end, the head defining a first ridge and a second ridge that is spaced from the first ridge along the distal direction, and a groove disposed between the first and second ridges, the groove being unthreaded and recessed into the head toward the central axis between the first and second ridges, wherein the groove is configured to receive at least part of the portion of the inner wall such that the first and second ridges couple the bone fixation element to the bone implant;

wherein the first ridge is convex with respect to the central axis and has a first ridge apex;

wherein the second ridge is convex with respect to the central axis and has a second ridge outer surface comprising a second threaded region that is configured to threadingly engage the first threaded region;

wherein the bone fixation element is configured such that the bone fixation element can be inserted through the at least one aperture with the second threaded region disengaged from, and spaced in the distal direction from, the first threaded region, and the first threaded region being positioned adjacent the groove and spaced in the distal direction from the first ridge apex.

2. The bone fixation system of claim 1, wherein the first ridge is unthreaded.

3. The bone fixation system of claim 1, wherein the inner wall includes a second curved portion in the longitudinal direction.

4. The bone fixation system of claim 3, wherein the first threaded region extends along the second curved portion.

5. The bone fixation system of claim 1, wherein the inner wall includes a linear portion that extends between the first threaded region and the upper surface.

6. The bone fixation system of claim 1, wherein the first and second wire segments each have a substantially circular cross section, wherein a first portion of the first wire defines a first side of the at least one aperture and a second portion of the second wire defines a second side of the at least one aperture.

7. The bone fixation system of claim 1, wherein the first ridge defines a first cross-sectional dimension, and the second ridge defines a second cross-sectional dimension that is no greater than the first cross-sectional dimension.

8. The bone fixation system of claim 1, wherein at least a portion of the groove is curved along the distal direction.

9. The bone fixation system of claim 1, wherein the groove is concave.

10. The bone fixation system of claim 1, wherein at least a portion of the groove is linear along the distal direction.

11. The bone fixation system of claim 1, wherein the groove is configured such that when the bone fixation element is inserted into the at least one aperture, the groove and the inner wall define a gap extending therebetween.

12. A bone fixation system comprising:

a bone plate defining a first end and a second end spaced from the first end along a longitudinal direction, the bone plate including a plate body that defines an upper surface, a bone-facing surface opposite the upper surface and spaced from the upper surface along a transverse direction that is perpendicular to the longitudinal direction, the bone plate comprising a first and a second wire segment, wherein each of the first and second wire segments are curved along the longitudinal direction and each have an inner wall, the inner wall of the first and second wire segments forms a plurality of apertures each extending through the plate body, and a portion of the inner wall of each of the first and second wire segments forming each of the plurality of apertures is curved along the transverse direction to define a convexly shaped outer surface having a first threaded region extending along the transverse direction; and a plurality of bone fixation elements each configured to be inserted at least partially through one of the apertures and into an underlying bone, each of the bone fixation elements defining a proximal end and a distal end spaced from the proximal end along a central axis in a distal direction, and each of the bone fixation elements defining a bone fixation body having a head disposed at the proximal end and a shaft that extends relative to the head toward the distal end, wherein the head defines a first ridge and a second ridge that is spaced from the first ridge along the distal direction, and an unthreaded groove disposed between the first and second ridges, the groove recessed into the head toward the central axis between the first and second ridges, wherein the groove is configured to receive at least part of the portion of the inner wall so as to secure the bone fixation element to the bone implant;

wherein the first ridge of each of the bone fixation elements is convex with respect to the central axis and has a first ridge apex;

wherein the second ridge of each of the bone fixation elements is convex with respect to the central axis and has a second ridge outer surface comprising a second threaded region that is configured to threadingly engage the first threaded region;

wherein each of the bone fixation elements is configured such that the bone fixation element can be inserted through at least one of the apertures with the second threaded region disengaged from, and spaced in the distal direction from, the first threaded region, and the first threaded region being positioned adjacent the unthreaded groove and spaced in the distal direction from the first ridge apex.

13. The bone fixation system of claim 12, wherein the inner wall defines a protrusion, the first threaded region is disposed on at least a portion of the protrusion.

14. The bone fixation system of claim 13, wherein the inner wall defines a first recess that extends from the upper surface to the protrusion along the transverse direction, and a second recess that extends from the bone-facing surface to the protrusion along the transverse direction, wherein the first and second recesses are configured to receive the first and second ridges respectively.

15. The bone fixation system of claim 12, wherein at least a portion of the groove is linear along the transverse direction.

16. The bone fixation system of claim 12, wherein at least a portion of the groove is threaded.

* * * * *